United States Patent [19]

Whitfield et al.

[11] Patent Number: 5,700,271
[45] Date of Patent: Dec. 23, 1997

[54] APPARATUS FOR APPLYING SURGICAL CLIPS

[75] Inventors: Kenneth H. Whitfield, New Haven; Ernie Aranyi, Easton, both of Conn.

[73] Assignee: United States Surgical Corporation, Norwalk, Conn.

[21] Appl. No.: 546,430

[22] Filed: Oct. 20, 1995

[51] Int. Cl.$^6$ ................................................ A61B 17/00
[52] U.S. Cl. .......................... 606/143; 606/139; 227/901
[58] Field of Search .................................. 606/139, 142, 606/143, 151; 227/901

[56] References Cited

U.S. PATENT DOCUMENTS

| | | |
|---|---|---|
| 2,968,041 | 1/1961 | Skold . |
| 3,777,538 | 12/1973 | Weatherly et al. . |
| 4,027,510 | 6/1977 | Hiltebrandt . |
| 4,084,594 | 4/1978 | Mosior . |
| 4,152,920 | 5/1979 | Green . |
| 4,166,466 | 9/1979 | Jarvik . |
| 4,226,242 | 10/1980 | Jarvik . |
| 4,242,902 | 1/1981 | Green . |
| 4,246,903 | 1/1981 | Larkin . |
| 4,296,751 | 10/1981 | Blake, III et al. . |
| 4,316,468 | 2/1982 | Klieman et al. . |
| 4,425,915 | 1/1984 | Ivanov . |
| 4,430,997 | 2/1984 | DiGiovanni et al. . |
| 4,509,518 | 4/1985 | McGarry et al. . |
| 4,534,351 | 8/1985 | Rothfuss et al. . |
| 4,557,263 | 12/1985 | Green ............................. 606/143 |
| 4,562,839 | 1/1986 | Blake, III et al. . |
| 4,576,166 | 3/1986 | Montgomery et al. . |
| 4,598,711 | 7/1986 | Deniega . |
| 4,646,740 | 3/1987 | Peters et al. . |
| 4,712,549 | 12/1987 | Peters et al. . |
| 4,850,355 | 7/1989 | Brooks et al. . |
| 5,030,226 | 7/1991 | Green et al. . |
| 5,049,152 | 9/1991 | Simon et al. . |
| 5,282,807 | 2/1994 | Knoepfler ......................... 606/143 |

FOREIGN PATENT DOCUMENTS

| | | |
|---|---|---|
| 0622048 | 11/1994 | European Pat. Off. . |
| 0671148 | 9/1995 | European Pat. Off. . |
| 94 13 296.8 | 11/1994 | Germany . |
| WO89/10094 | 11/1989 | WIPO . |

*Primary Examiner*—Jeffrey A. Schmidt

[57] ABSTRACT

A surgical clip applying instrument is disclosed which includes a handle portion having a first handle and a second handle mounted for relative movement. The handles define a single closing stroke between an open position and a closed position. The closing stroke includes an initial throw, an intermediate throw, and a final throw. The clip applying instrument includes body portion extending distally from the handle portion and defining a longitudinal axis, and a plurality of surgical clips disposed within the body portion. A jaw assembly including first and second jaw portions is mounted at the distal end portion of the body portion and is movable between an approximated position and a spaced position. A jaw control mechanism is configured to move the jaw portions to the spaced position for reception of a distalmost clip in response to the initial throw of the handles. The jaw control mechanism is configured to maintain the jaw portions in the spaced position during the intermediate throw of the handles. In addition, the jaw control mechanism is configured to move the jaw assembly to the approximated position to deform the distalmost clip in response to the final throw of the handles. A clip advancer is also provided to individually distally advance the distalmost clip to the jaw assembly during the intermediate throw of the handles. A method for assembly of a surgical instrument is also disclosed.

25 Claims, 26 Drawing Sheets

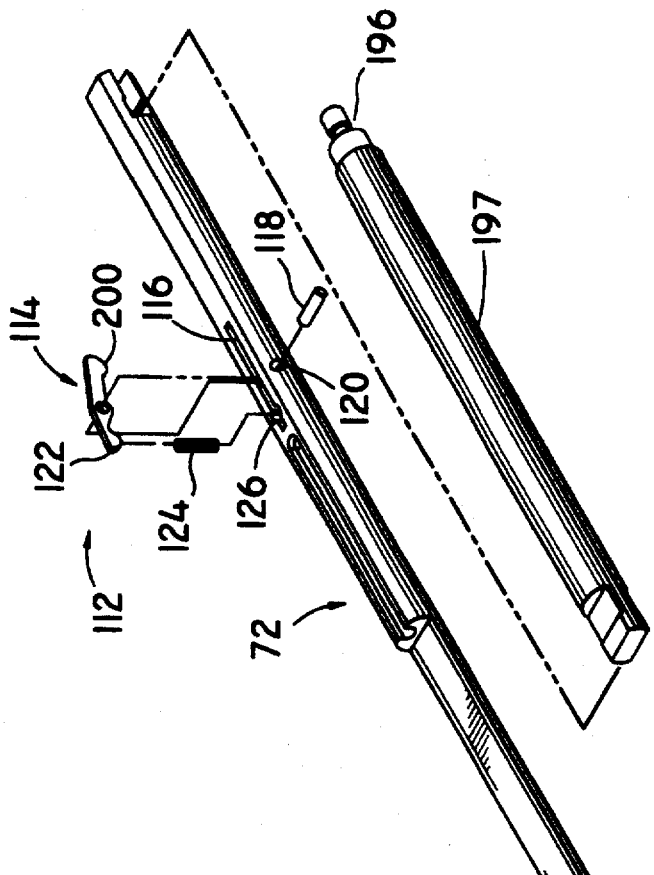
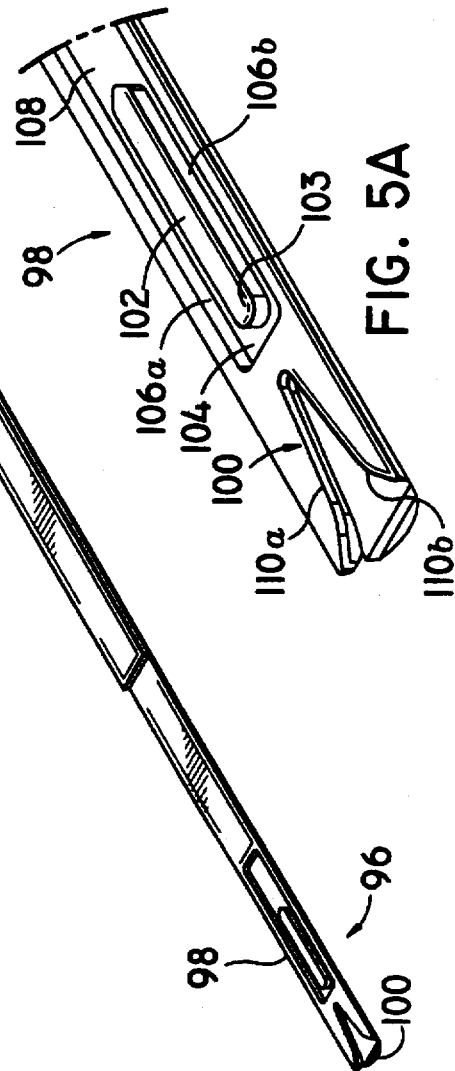
FIG. 5
FIG. 5A

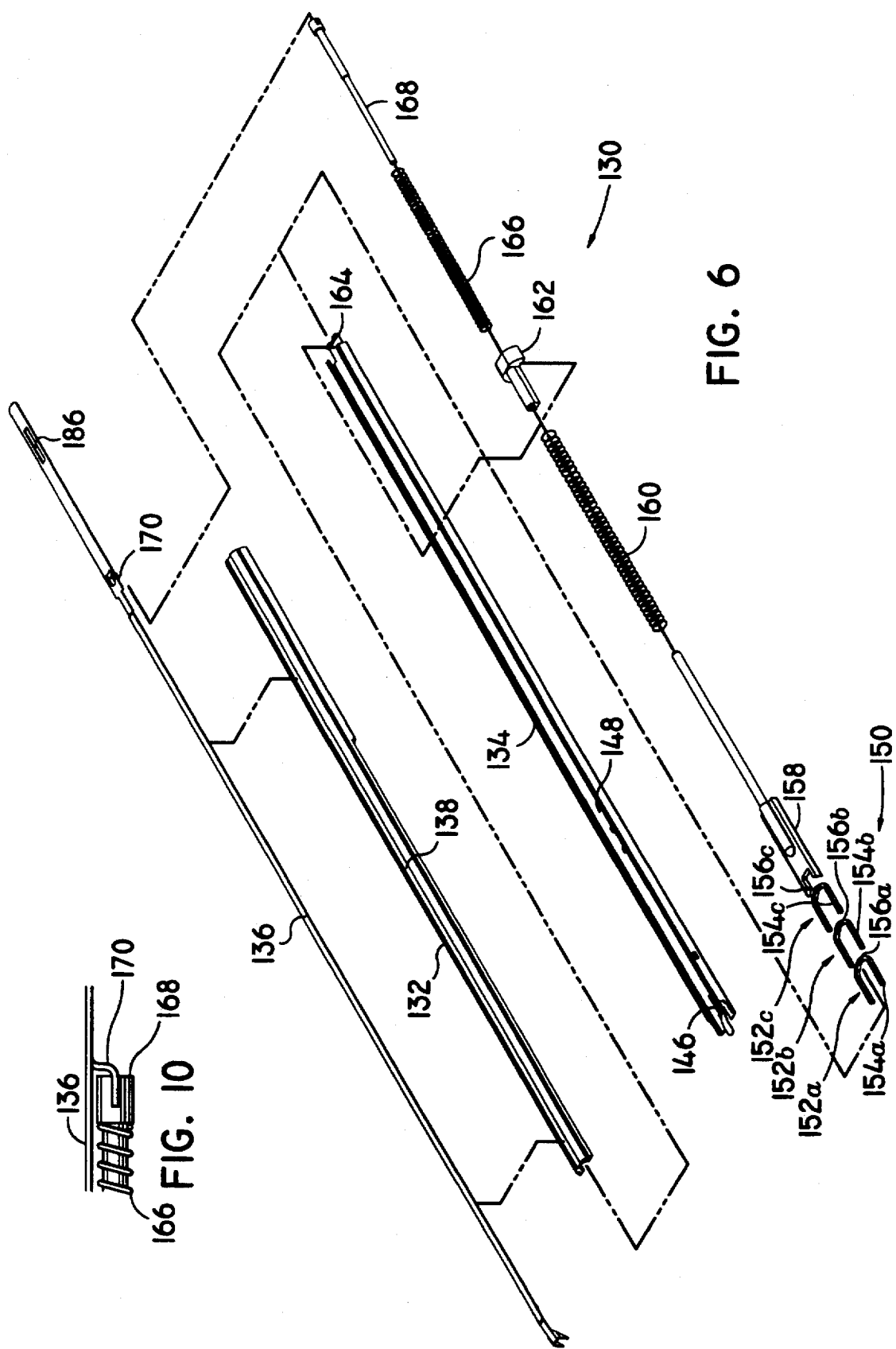

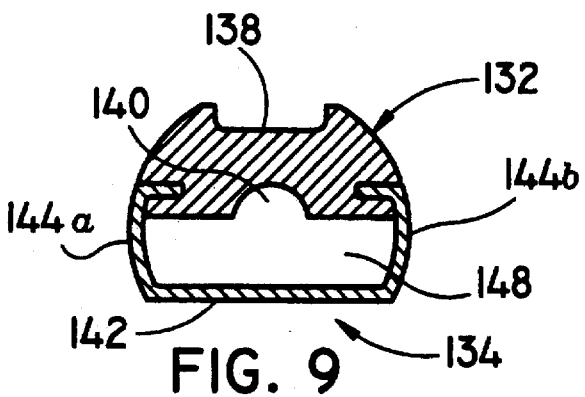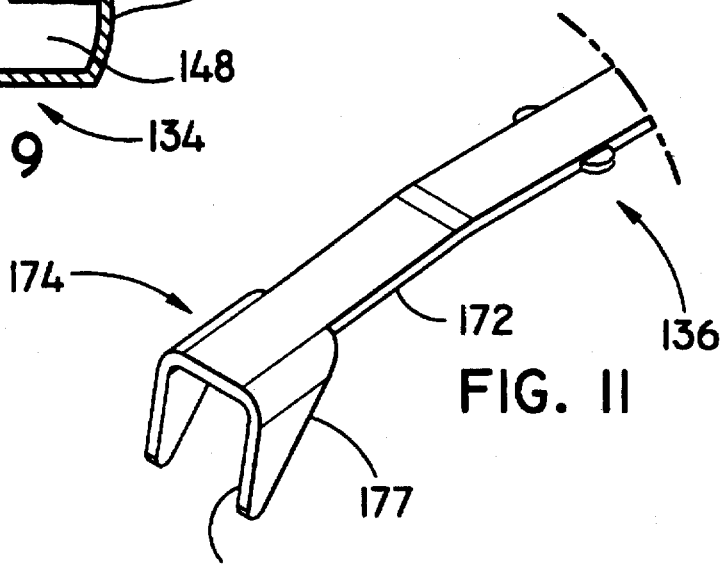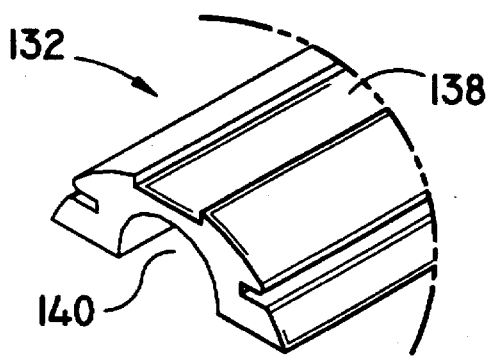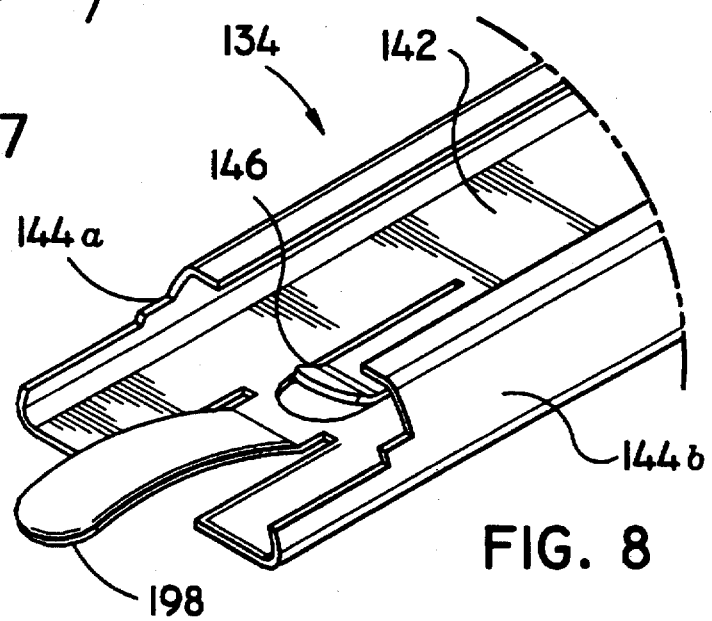

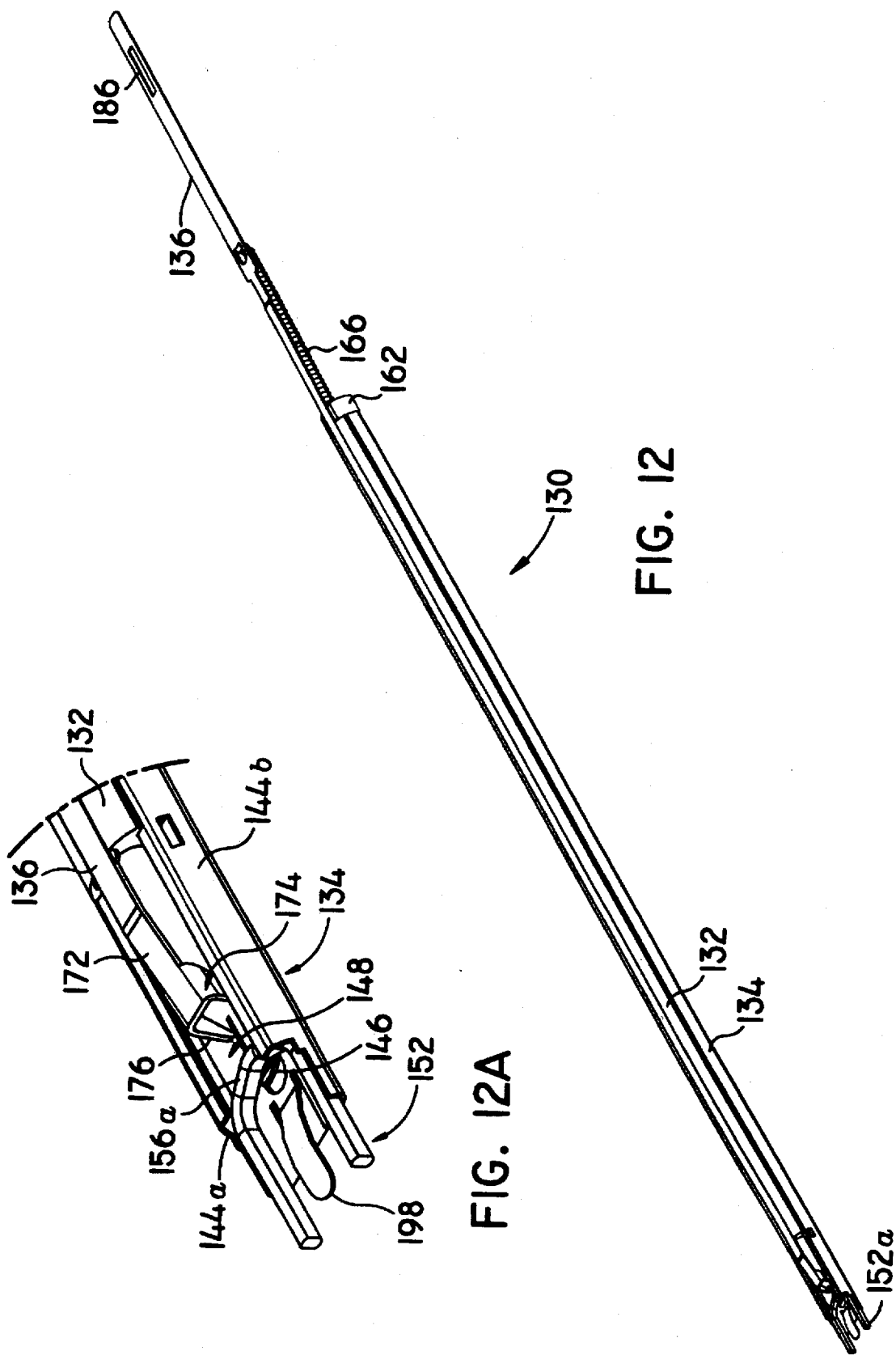

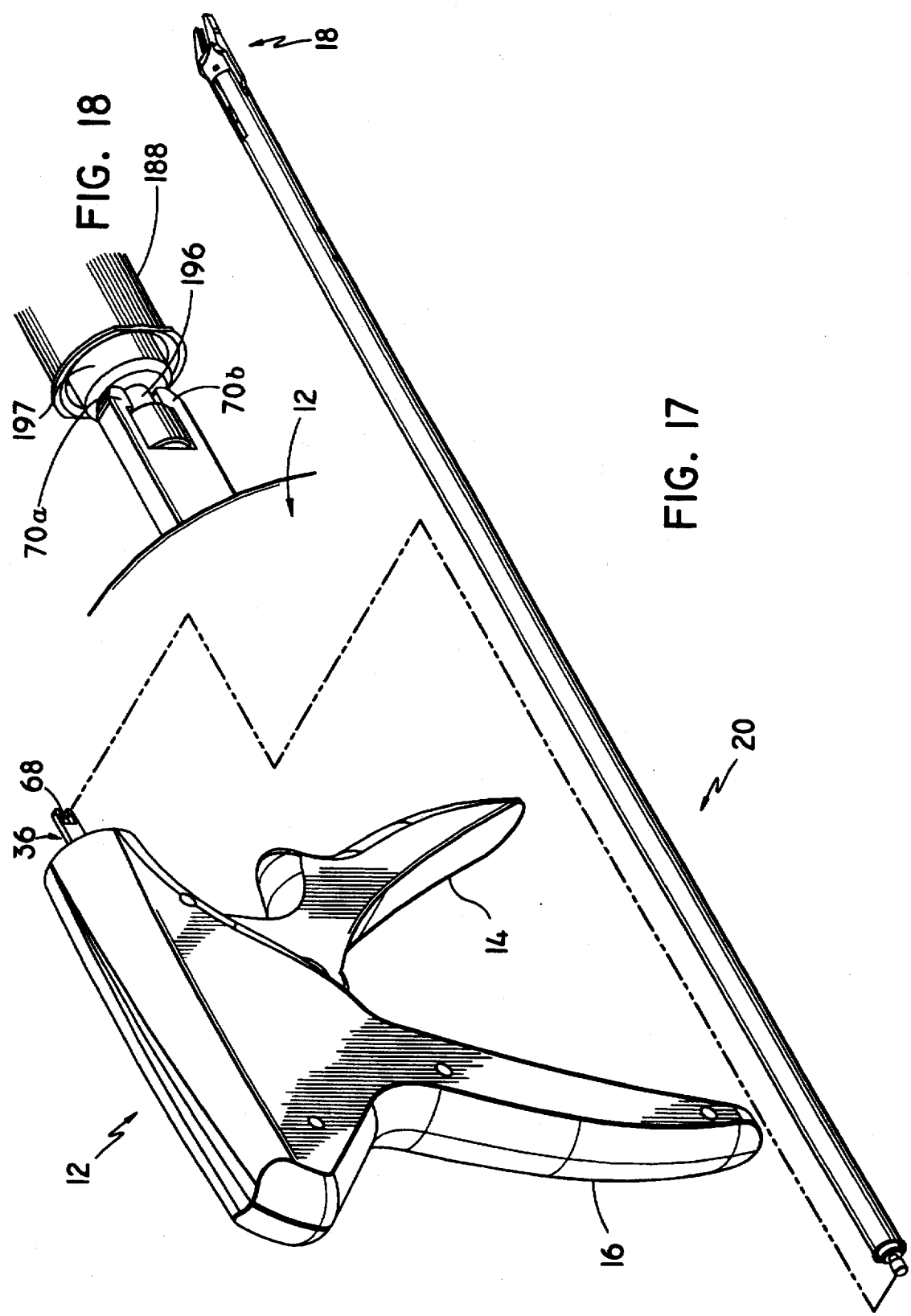

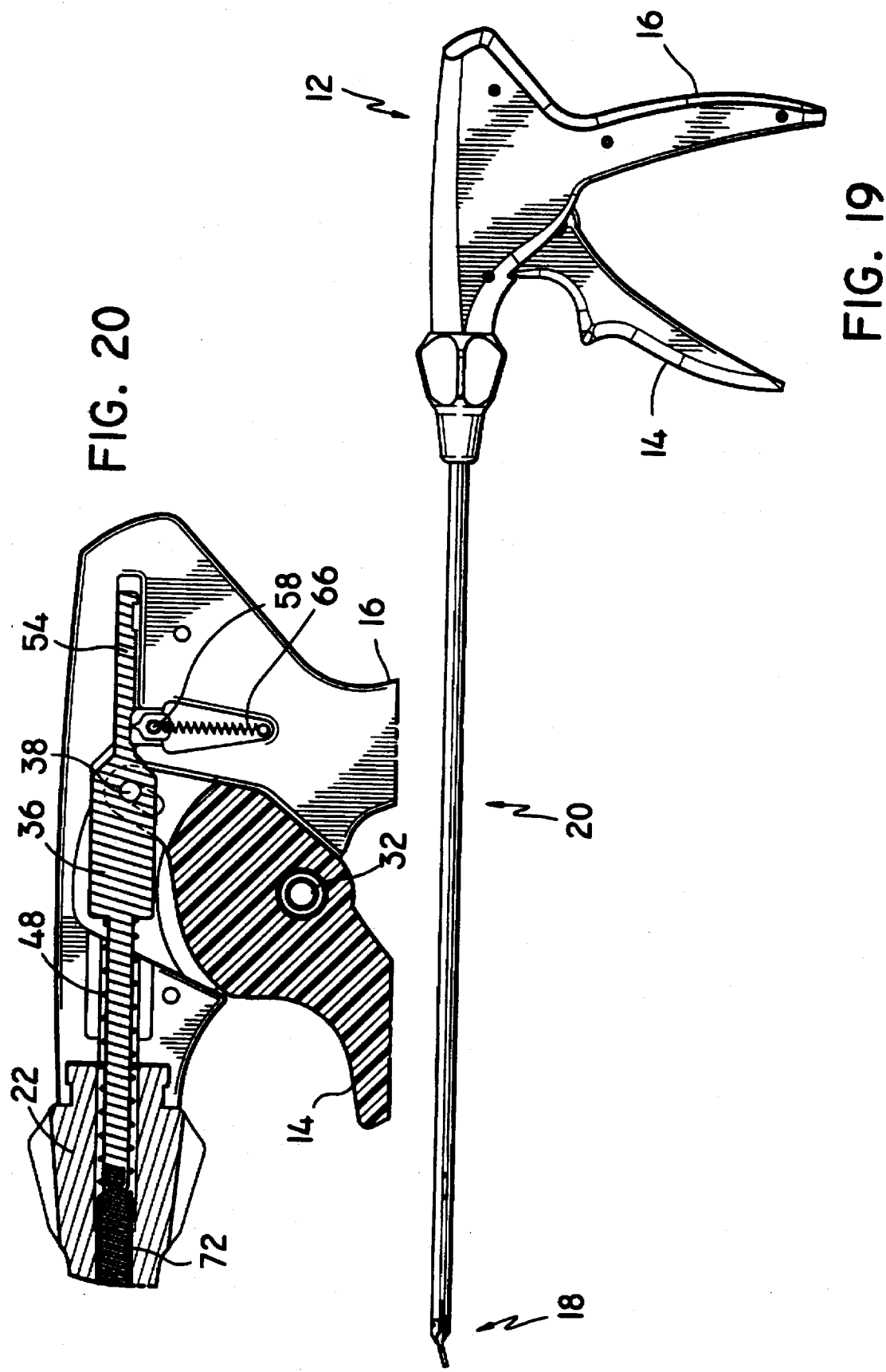

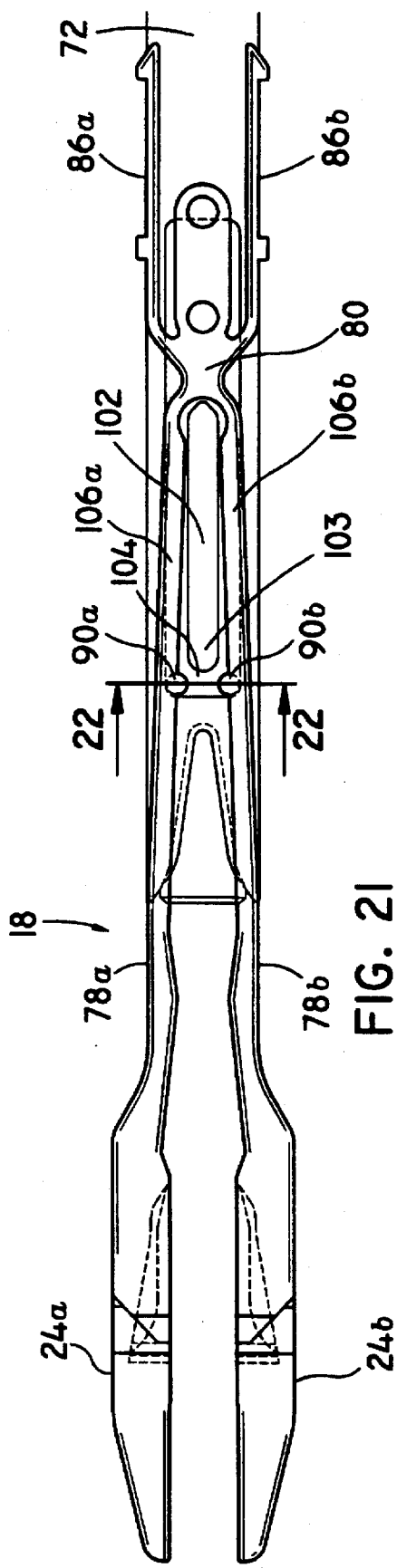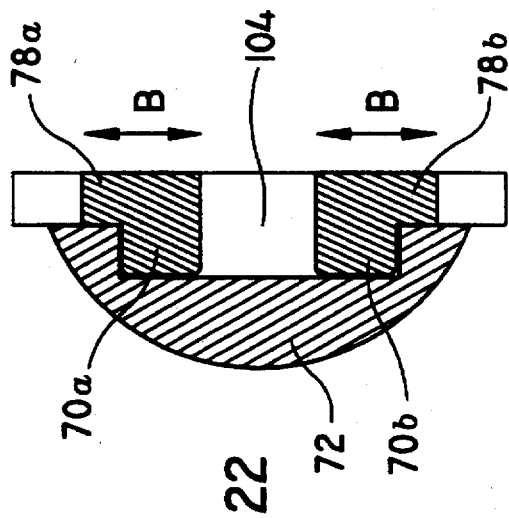
FIG. 21
FIG. 22

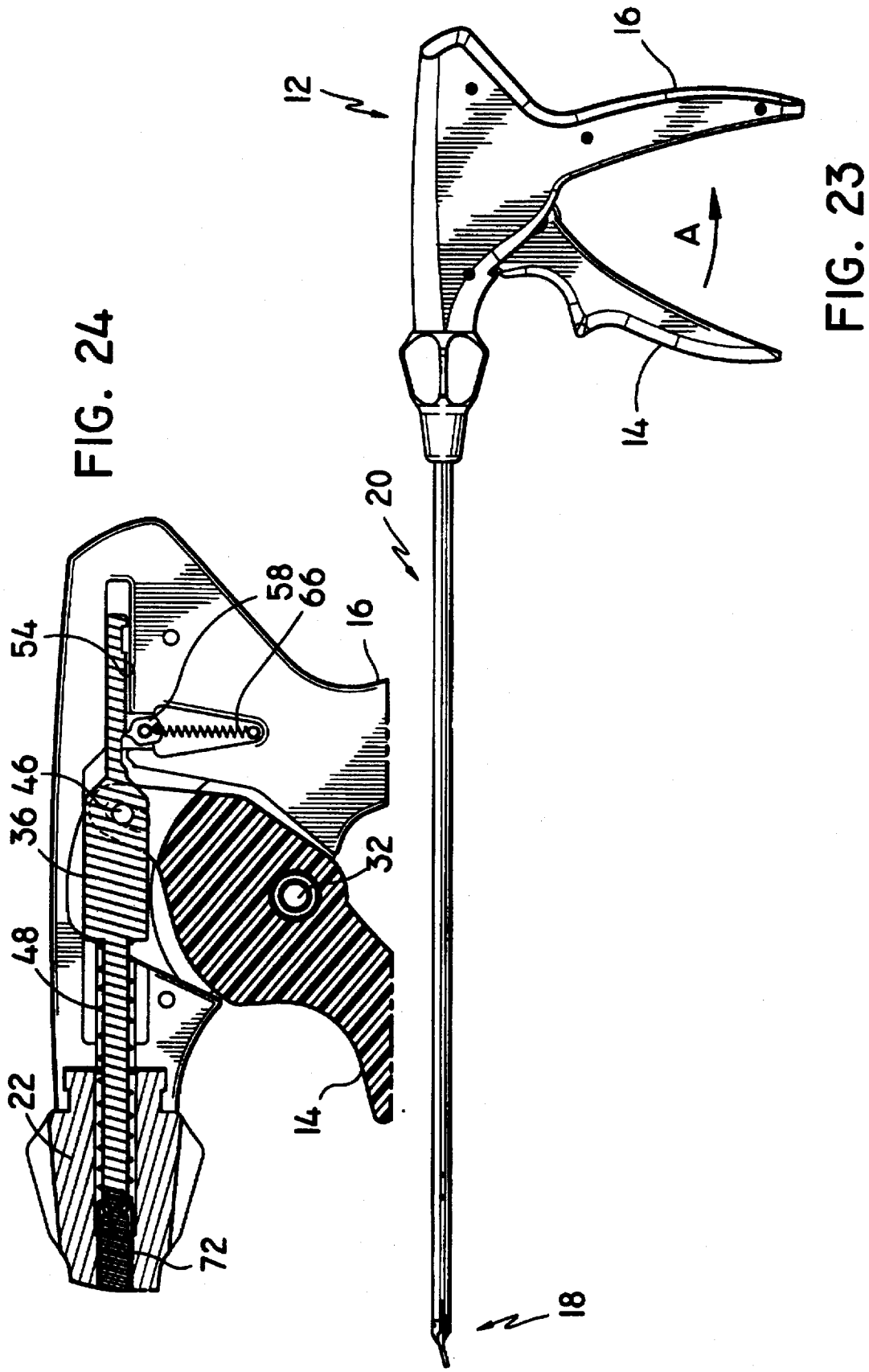

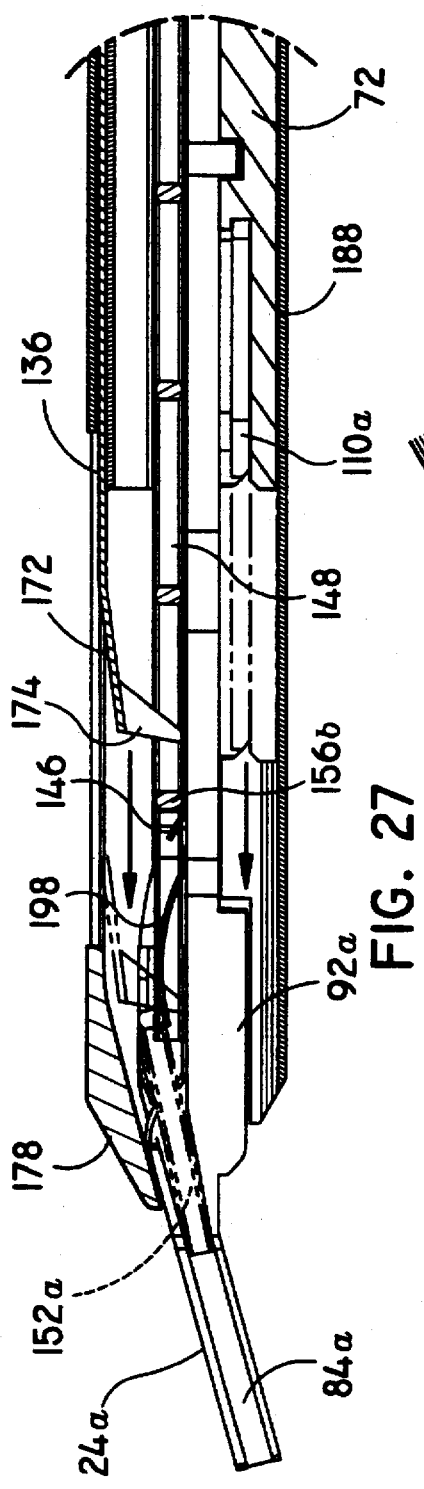
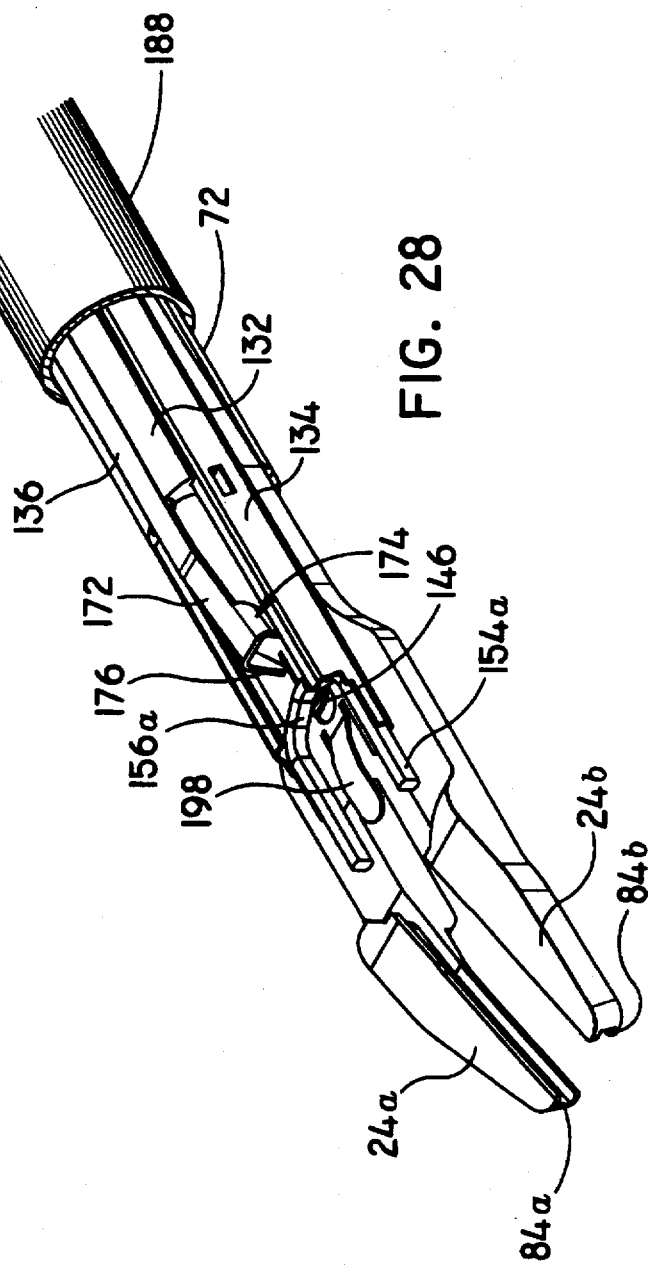

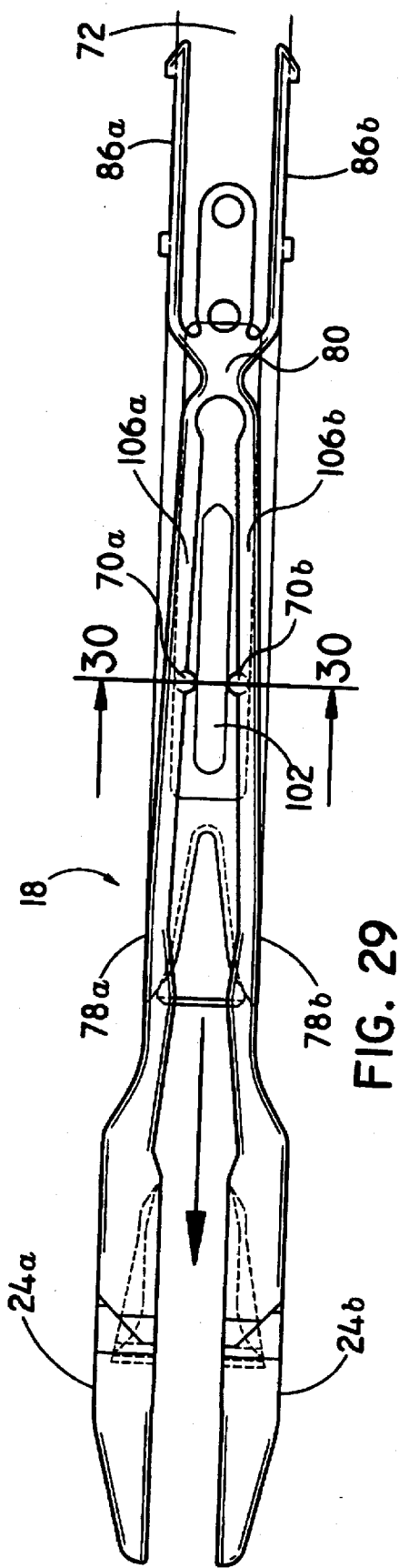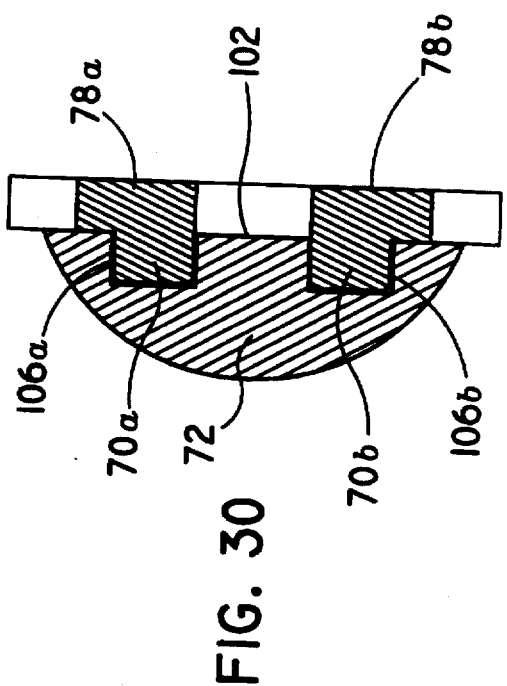

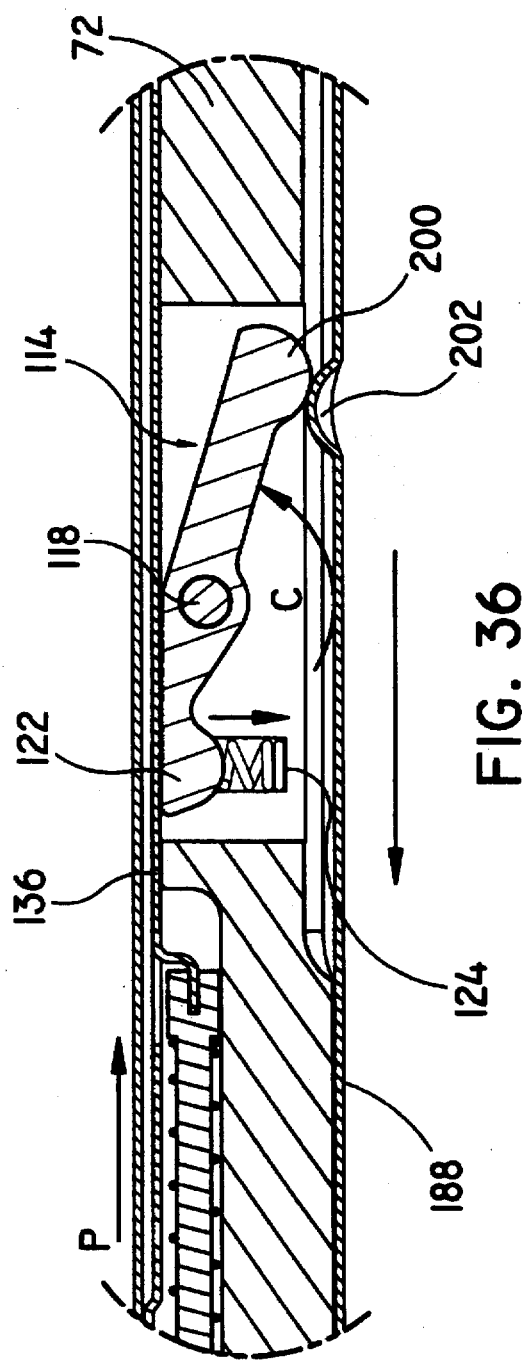
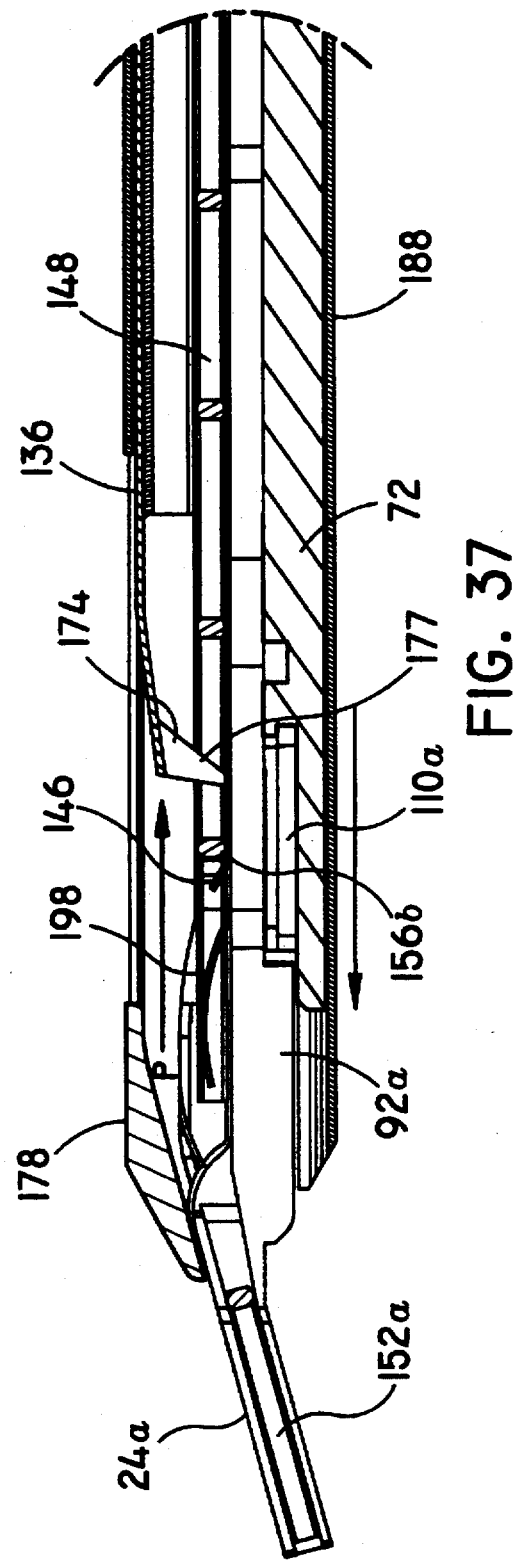

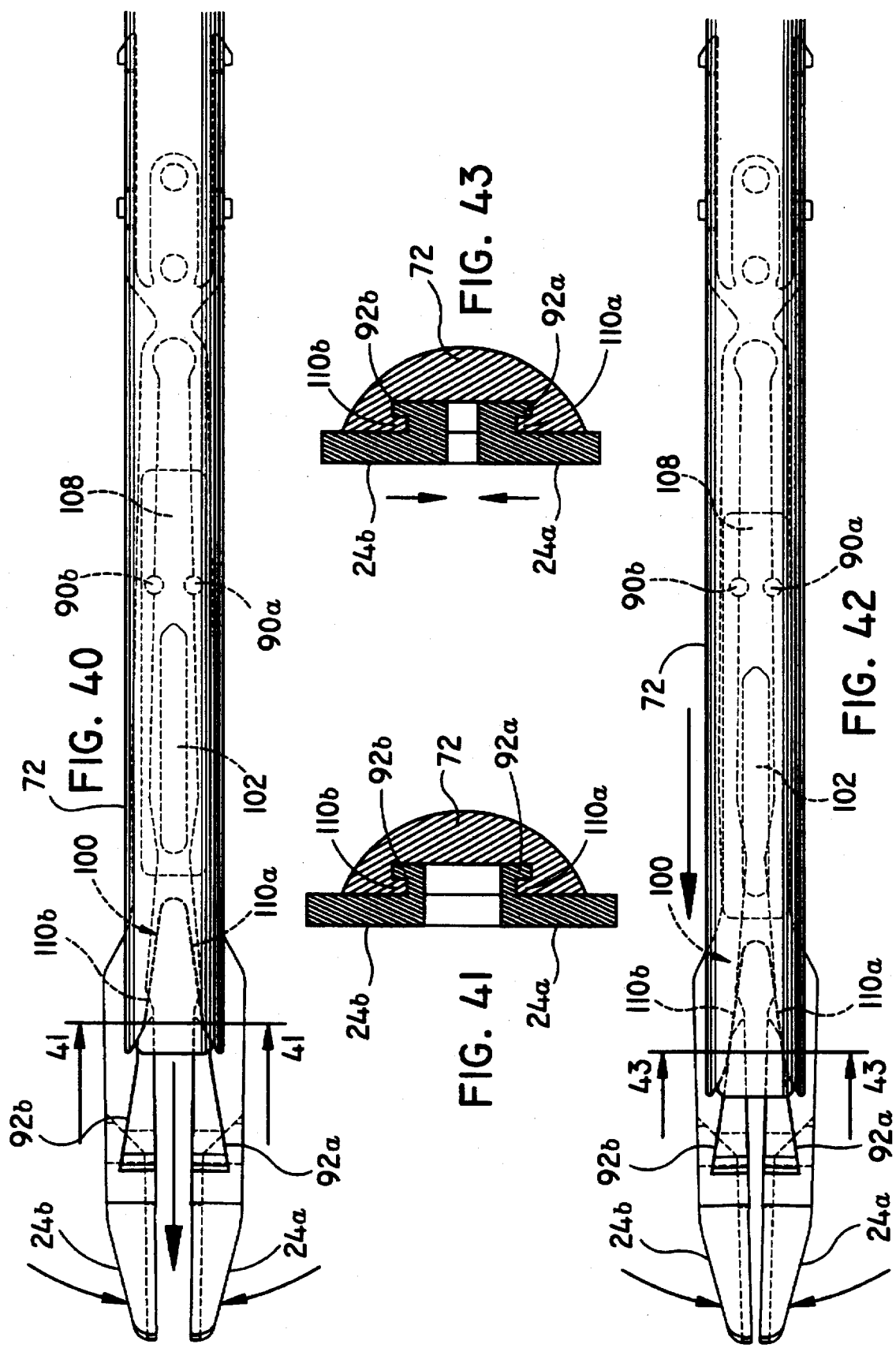

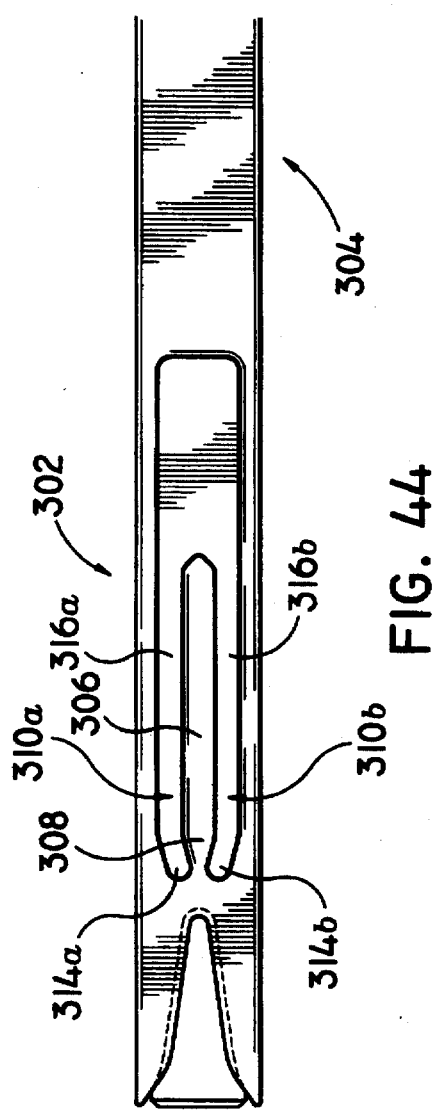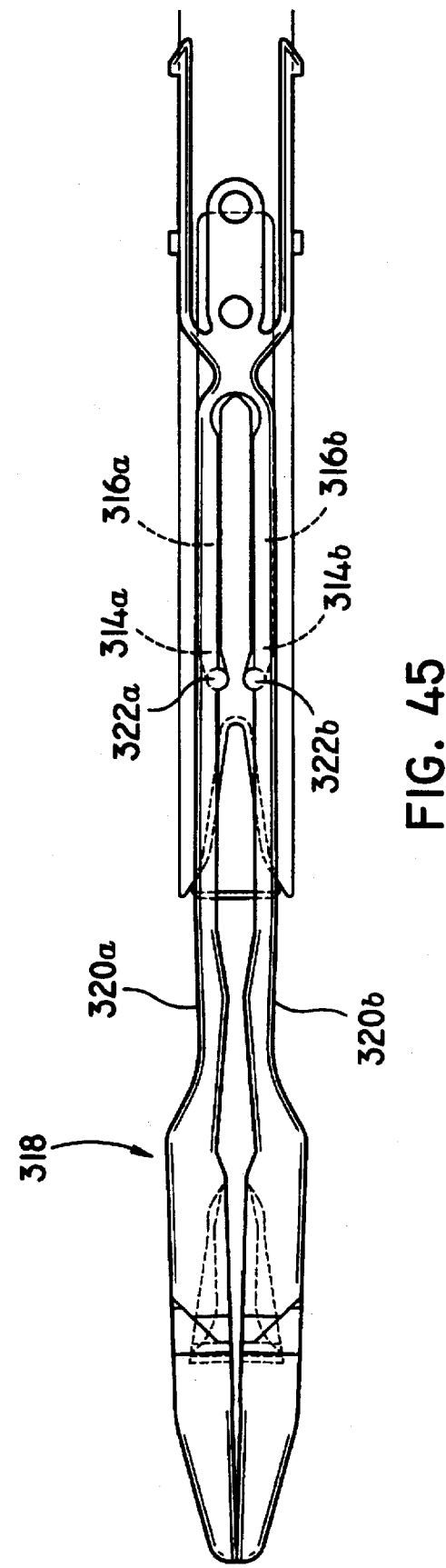

APPARATUS FOR APPLYING SURGICAL CLIPS

BACKGROUND

1. Technical Field

The present disclosure relates to apparatus for applying surgical clips to body tissue. In particular, the disclosure relates to surgical clip appliers configured to be inserted through relatively narrow access devices such as those used in laparoscopic or endoscopic procedures.

2. Description of the Related Art

Laparoscopic procedures are performed in the interior of the abdomen through a small incision, e.g., through narrow endoscopic tubes or cannulas inserted through a small entrance incision in the skin. Minimally invasive procedures performed elsewhere in the body are often generally referred to as "endoscopic" procedures. Typically in such procedures, a tube or cannula device is extended into the patient's body through the entrance incision to provide an access port which allows insertion of various surgical instruments therethrough. These instruments are used for performing surgical procedures on organs, blood vessels, ducts, or body tissue far removed from the incision. Often during these procedures, it is necessary to apply hemostatic clips to blood vessels or various ducts to prevent the flow of body fluids therethrough during the procedure.

Multiple endoscopic clip appliers (i.e., clip appliers that are able to apply multiple clips in endoscopic or laparoscipic procedures during a single entry into the body cavity) are described in commonly-assigned U.S. Pat. Nos. 5,084,057 and 5,100,420 to Green et al., the disclosures of which are hereby incorporated by reference herein. Other multiple endoscopic clip appliers are disclosed in commonly-assigned copending U.S. patent application Ser. Nos. 08/134,347, filed Oct. 8, 1993 by Pratt et al., now U.S. Pat. No. 5,607,436 and 08/515,341, filed Aug. 15, 1995 by Pier et al., the contents of which are also hereby incorporated by reference herein.

One advantage of minimally invasive surgical procedures is the reduction of trauma to the patient as a result of accessing internal organs through smaller incisions. Known multiple endoscopic clip appliers have greatly facilitated the advent of more advanced minimally invasive procedures by permitting multiple clip applications during a single entry into the body cavity. Commercially available multiple endoscopic clip appliers are generally of 10 mm outer diameter and are adapted to be introduced through a 10 mm cannula. As minimally invasive procedures continue to evolve and the advantages thereof are extended to additional clinical applications, it has become desirable to further reduce incision size(s) and therefore the size of all instrumentation introduced therethrough.

The structure of surgical instruments intended to perform numerous functions within a confined space is necessarily complex. Consequently, the assembly process for these instruments is often complicated and may involve numerous relatively small parts.

It is therefore desirable to maximize the ease with which such instruments may be assembled.

It is also desirable to provide a multiple endoscopic clip applier having structure which facilitates the application of surgical clips while further minimizing the required incision size at the surgical site.

SUMMARY

The subject disclosure is directed to a unique surgical clip applying instrument which includes a handle portion having first and second handles mounted for relative movement. The handles define a single closing stroke between an open position and a closed position. The closing stroke includes an initial throw, an intermediate throw, and a final throw. The clip applying instrument includes a body portion extending distally from the handle portion and defining a longitudinal axis, and a plurality of surgical clips disposed within the body portion.

A jaw assembly, including first and second jaw portions, is mounted at the distal end portion of the body portion and is movable between a substantially approximated position and a spaced position. A jaw control mechanism is provided which cooperates with the jaw assembly to effectuate movement thereof. In one embodiment, the jaw control mechanism is configured to move the jaw portions from the substantially approximated position to the spaced position for reception of a distalmost clip in response to the initial throw of the handles. In a second embodiment, the jaw control mechanism ensures that the jaw portions are in the spaced position for reception of a distalmost clip in response to the the initial throw of the handles.

The jaw control mechanism is configured to maintain the jaw portions in the spaced position during the intermediate throw of the handles. In addition, the jaw control mechanism is configured to move the jaw assembly to the substantially approximated position to deform the clip within the jaw assembly in response to the final throw of the handles. A clip advancer is also provided to individually distally advance a distalmost clip to the jaw assembly, preferably during the intermediate throw of the handles.

A method for assembly of a surgical instrument is also disclosed which includes providing a handle subassembly having a driver member mounted for longitudinal movement in response to actuation of the handle subassembly. An actuator subassembly is provided including a proximal mounting portion for engagement with the driver member and a distal mounting portion. A tool subassembly is provided having a proximal mounting portion configured to engage the distal mounting portion of the actuator subassembly. The actuator subassembly is assembled with the handle subassembly such that the proximal mounting portion of the actuator subassembly is in engagement with the driver member. The actuator subassembly is assembled with the tool subassembly such that the proximal mounting portion of the tool assembly is in engagement with the distal mounting portion of the actuator subassembly.

These and other features of the subject surgical apparatus will become more readily apparent to those skilled in the art from the following detailed description.

BRIEF DESCRIPTION OF THE DRAWINGS

Various embodiments of the subject surgical apparatus are described herein with reference to the drawings wherein:

FIG. 2A is an enlarged side view of the handle portion of the subject surgical clip applier, illustrating a preferred ratchet assembly;

FIG. 3A is an enlarged perspective view of the jaw assembly, illustrating position tabs formed on shank portions thereof;

FIG. 5 is a perspective view with parts separated of a preferred thrust bar;

FIG. 5A is an enlarged perspective view of camming structures formed on the distal end portion of the thrust bar;

FIG. 6 is a perspective view with parts separated of a preferred clip advancement subassembly;

FIG. 7 is an enlarged perspective view of the upper housing;

FIG. 8 is an enlarged perspective view of the lower housing;

FIG. 9 is an enlarged cross-sectional view of a feed chute formed by the attachment of the upper housing and the lower housing;

FIG. 10 is an enlarged side view of a return spring attachment to a preferred clip pusher;

FIG. 11 is an enlarged perspective view of the distal end of the clip pusher, illustrating the clip engaging portion;

FIG. 12 is a perspective view of a preferred clip advancement subassembly;

FIG. 12A is an enlarged perspective view of the distal end portion of the clip advancement subassembly, illustrating the lower housing, clip pusher, and a surgical clip;

FIG. 17 is a perspective view of the subject surgical clip applier with the endoscopic portion separated from the handle portion;

FIG. 18 is an enlarged perspective view illustrating the junction of the handle portion and the endoscopic portion;

FIG. 19 is a side view of the subject surgical clip applier, illustrating a movable handle in the open position;

FIG. 20 is an enlarged cross-sectional view of the handle portion in the open position;

FIG. 21 is a plan view from above illustrating the relative position of the jaw assembly and the thrust bar when the position tabs are disposed in a distal cavity;

FIG. 22 is an enlarged cross-sectional view taken along line 22—22 of FIG. 21, illustrating the position tabs disposed in the distal cavity;

FIG. 23 is a side view of the subject surgical clip applier, illustrating the movable handle at the beginning of the intermediate throw of the closing stroke;

FIG. 24 is an enlarged cross-sectional view of the handle portion of the instrument in the progressive actuation position of FIG. 23;

FIG. 27 is an enlarged cross-sectional view of the jaw assembly, illustrating the advancement of a surgical clip into the jaw portions of the instrument in the progressive actuation position of FIG. 23;

FIG. 28 is an enlarged perspective view of the jaw assembly prior to advancement of a-surgical clip by the clip pusher;

FIG. 29 is a plan view from above illustrating the relative position of the jaw assembly and the thrust bar when the position tabs are disposed in preferred longitudinally elongated parallel channels;

FIG. 30 is an enlarged cross-sectional view taken along line 30—30 of FIG. 29, illustrating the position tabs disposed in the parallel channels;

FIG. 36 is an enlarged cross-sectional view of the endoscopic portion, illustrating the trip lever pivoting out of engagement with the clip pusher;

FIG. 37 is an enlarged cross-sectional view of the jaw assembly, illustrating the clip pusher moving proximally with the return spring;

FIG. 40 is a plan view from below, illustrating the relative position of the jaw assembly and the thrust bar as camming surfaces on the thrust bar begin to approximate the jaw portions;

FIG. 41 is an enlarged cross-sectional view taken along line 41—41 of FIG. 40, illustrating camming surfaces of the jaw assembly and the thrust bar;

FIG. 42 is a plan view from below, illustrating the relative positions of the jaw assembly and the thrust bar as camming surfaces on the thrust bar approximate the jaw portions;

FIG. 43 is an enlarged cross-sectional view taken along line 43—43 of FIG. 42, illustrating camming surfaces of the jaw assembly and the thrust bar;

FIG. 44 is a plan view from above of the thrust bar of another preferred embodiment of the surgical clip applier of the subject disclosure;

FIG. 45 is a plan view from above of the embodiment of FIG. 44, illustrating the relative position of the jaw assembly and the thrust bar when position tabs are disposed in angled camming slots;

DETAILED DESCRIPTION OF PREFERRED EMBODIMENTS

Figure 1:
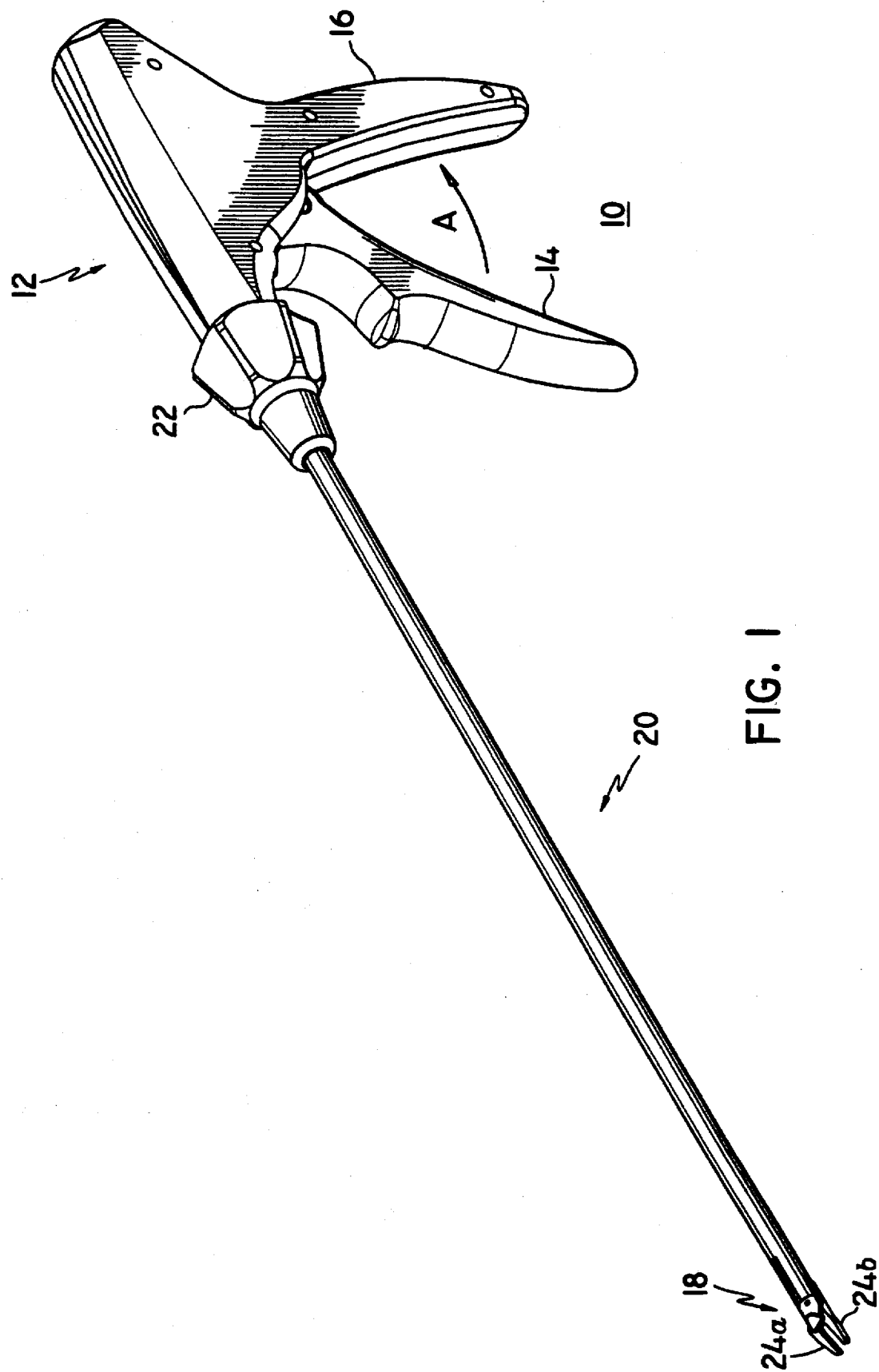
FIG. 1 is a perspective view of a surgical clip applier constructed in accordance with a preferred embodiment of the subject disclosure.

The preferred embodiments of the apparatus disclosed herein will be discussed in terms of endoscopic procedures and apparatus. However, use herein of terms such as "endoscopic" should not be construed to limit the present application to an apparatus for use in conjunction with an endoscopic tube. In addition, it is believed that the present apparatus may find use in laparoscopic or arthroscopic surgery wherein access to the surgical site is achieved through a narrow cannula, or a small incision.

In the drawings and in the description which follows, the term "proximal," as is traditional, will refer to the end of the apparatus which is closest to the operator, while the term "distal" will refer to the end which is furthest from the operator.

Referring now in detail to the drawings in which like reference numerals identify similar or identical elements, a preferred embodiment of the clip applying instrument of the subject disclosure is illustrated in FIG. 1, and is designated generally by reference numeral 10. Clip applying instrument 10 includes handle portion 12 having pivoting or movable handle 14 and stationary handle 16. Manipulation of these handles 14, 16 actuates a tool assembly, such as jaw assembly 18, through elongated body portion 20. The junction at which body portion 20 is joined to handle portion 12 includes fluted rotation collar 22 for remotely varying the orientation of jaw assembly 18 relative to the surgical site. Jaw assembly 18 includes first and second juxtaposed jaw portions 24a and 24b, which are simultaneously movable between a substantially approximated configuration in which jaw portions 24a and 24b are in relatively close relation to one another and a spaced configuration in which jaw portions 24a and 24b are separatable at least a sufficient distance to receive a surgical clip therebetween.

With continued reference to FIG. 1, movable handle 14 is shown in a fully open or "at-rest" position with respect to handle 16. Pivoting movement of movable handle 14 with respect to stationary handle 16 in the direction of arrow "A" from the open position to the closed position defines a closing stroke. During this closing stroke, jaw portions 24a and 24b are cammed open to a spaced configuration to receive a surgical clip. Upon further pivoting of movable handle 14, jaw portions 24a and 24b are maintained in the spaced configuration and the distalmost surgical clip is advanced between the spaced apart jaw portions. Final pivoting of movable handle 14 approximates jaw portions 24a and 24b to deform the clip.

The subject surgical clip applier 10 will be described with respect to various subassemblies. In particular, the surgical clip applier 10 includes subassemblies for handle portion 12, jaw assembly 18, thrust bar 72, and a clip advancement structure 130. For manufacturing economy, each of these subassemblies can be individually completed at separate workstations. Subsequently, the finished subassemblies may be put together in a final assembly procedure as will be described in greater detail below.

The Handle Portion Subassembly

Figure 2:
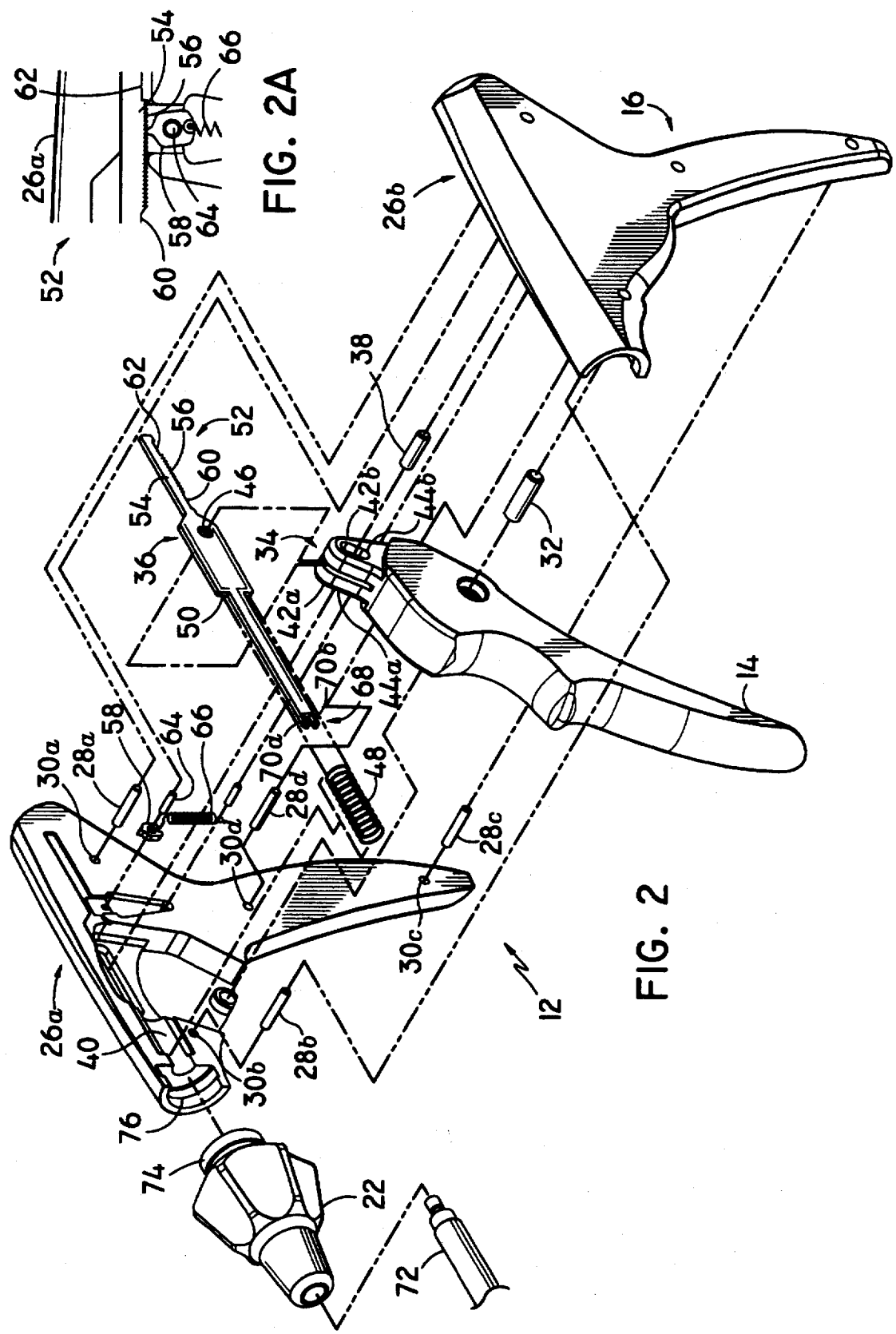
FIG. 2 is a perspective view with parts separated of the handle portion of the surgical clip applier of FIG. 1.

FIG. 2 illustrates the components of handle portion 12 of instrument 10. Handle portion 12 includes left and right housing portions 26a and 26b respectively, in which the components of the handle portion are positioned. Housing portions 26a and 26b are positioned by pins 28a, 28b, 28c and 28d inserted within apertures 30a, 30b, 30c and 30d, and secured together by sonic welding or other known means. Movable handle 14 is mounted to housing portions 26a and 26b by pin 32 which permits pivotal motion of handle 14 with respect to stationary handle 16.

Movable handle 14 further includes clevis 34 connected to a driver member, such as pusher plate 36, by means of pin connector 38. Pusher plate 36 is mounted within longitudinal stepped bore 40 defined in housing portions 26a and 26b for reciprocal longitudinal motion therein. Clevis 34 includes a pair of spaced apart shackles 42a and 42b, each of which has an elongated aperture 44a and 44b defined therethrough for reception of pin connector 38, which is slidable therein. This sliding arrangement permits the user to exert varying levels of torque on the jaw assembly 18 depending upon the position of pivoting handle 14 with respect to stationary handle 16. In particular, greater torque may be necessary to close jaw portions 24a and 24b to deform a clip on a blood vessel than to cam open the jaw portions or to advance a clip to the jaw assembly.

Pusher plate 36 is operatively connected to the jaw assembly as will be described below. Pusher plate 36 may be stamped or machined from a single piece of sheet metal or rigid engineering plastic. Pusher plate 36 includes an aperture 46 for the reception of pin connector 38. Return spring 48, configured to engage shoulder portion 50 of pusher plate 36, is provided to normally bias pusher plate 36 proximally and thereby to normally bias movable handle 14 to the open position. Ratchet assembly 52 includes rack 54 having a plurality of ratchet teeth 56 formed on a proximal portion of pusher plate 36 and pawl 58 disposed in handle portion 12. Distal portion 60 and proximal portion 62 of rack 54 are devoid of ratchet teeth 56. Pawl 58 is rotatably mounted by pawl pin 64 and normally biased into engagement with the ratchet teeth of rack 54 by spring 66. As illustrated in FIG. 2A, each of the ratchet teeth 56 on rack 54 is shaped having a substantially vertical portion and a substantially sloping portion to permit incremental distal advancement of pusher plate 36 while restricting proximal movement of pusher plate 36.

With continued reference to FIG. 2, pusher plate 36 includes bifurcated distal portion 68 having prongs 70a and 70b which facilitate rotatable mounting to an actuator, such as thrust bar 72. Alternatively, pusher plate 36 and thrust bar 72 may be connected by any other known distal mounting structure including, e.g. a ball-and-socket arrangement.

Rotation collar 22 is operatively connected to thrust bar 72 and is angularly rotatable therewith. Rotation collar 22 includes annular flange portion 74 rotatably mounted within annular slot 76 formed in housing portion 26a and 26b.

Jaw Assembly Subassembly

Figure 3:
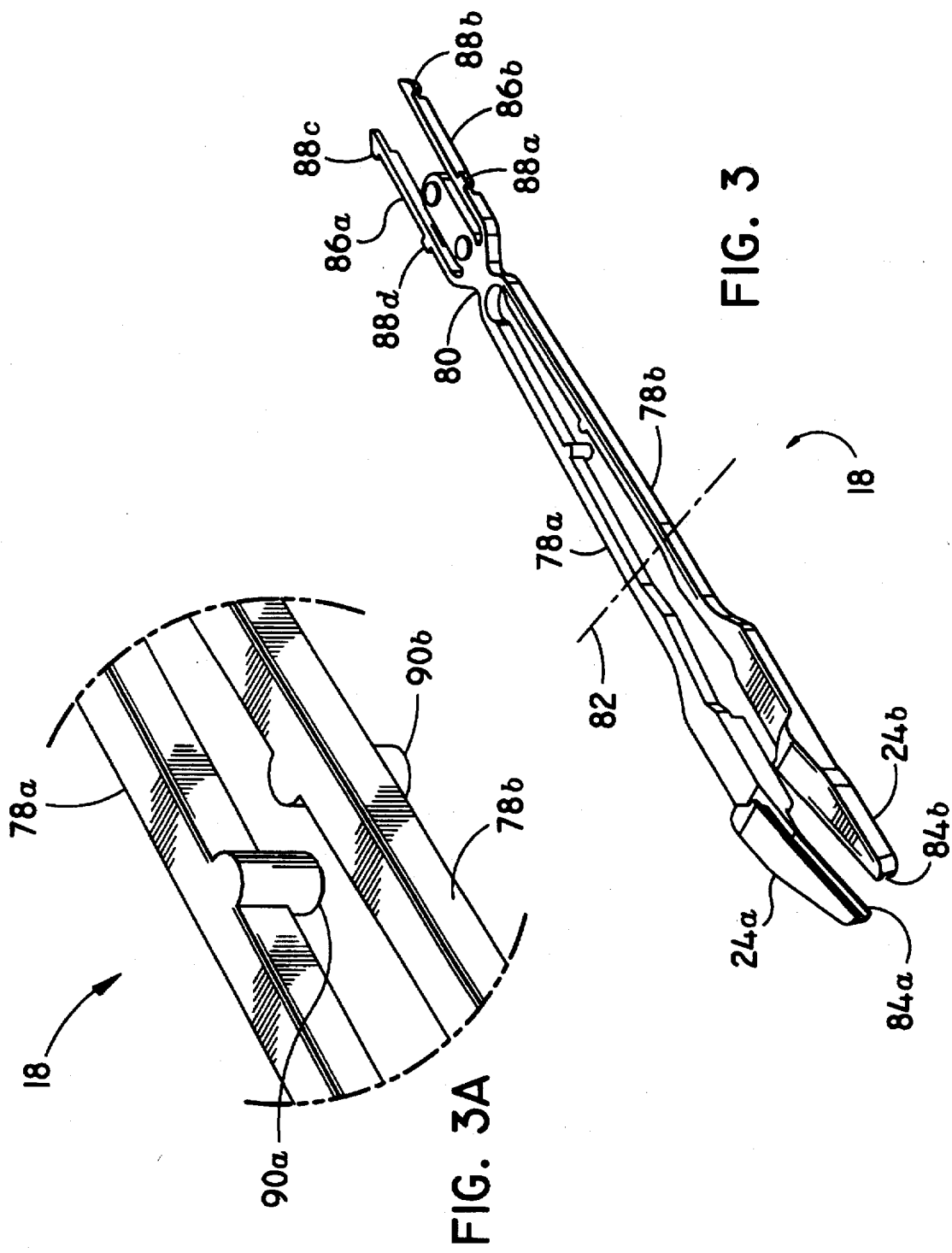
FIG. 3 is an enlarged perspective view of a preferred jaw assembly of the subject surgical clip applier.

With reference to FIG. 3, jaw assembly 18 includes elongated shank portions 78a and 78b connected at crown portion 80. Midline 82 is defined through each of shank portions 78a and 78b. The portion of jaw assembly 18 proximal to midline 82 constitutes the proximal portion of jaw assembly 18. The portion of jaw assembly 18 distal to midline 82 constitutes the distal portion of jaw assembly 18. Resilience in shank portions 78a and 78b permits relative approximation and spacing of juxtaposed jaw portions 24a and 24b. A pair of elongated channels 84a and 84b is provided on the inner surfaces of jaw portions 24a and 24b for reception of a surgical clip as will be described below. Jaw assembly 18 further includes proximal legs 86a and 86b, having a plurality of radially outwardly extending tabs 88a, 88b, 88c, and 88d formed thereon. These tabs are used for mounting and assembly as will be described in greater detail below.

FIG. 3A illustrates, in enlarged form, a pair of position tabs 90a and 90b disposed on elongated shank portions 78a and 78b respectively, to cam jaw portions 24a and 24b as will be described below.

Figure 4:
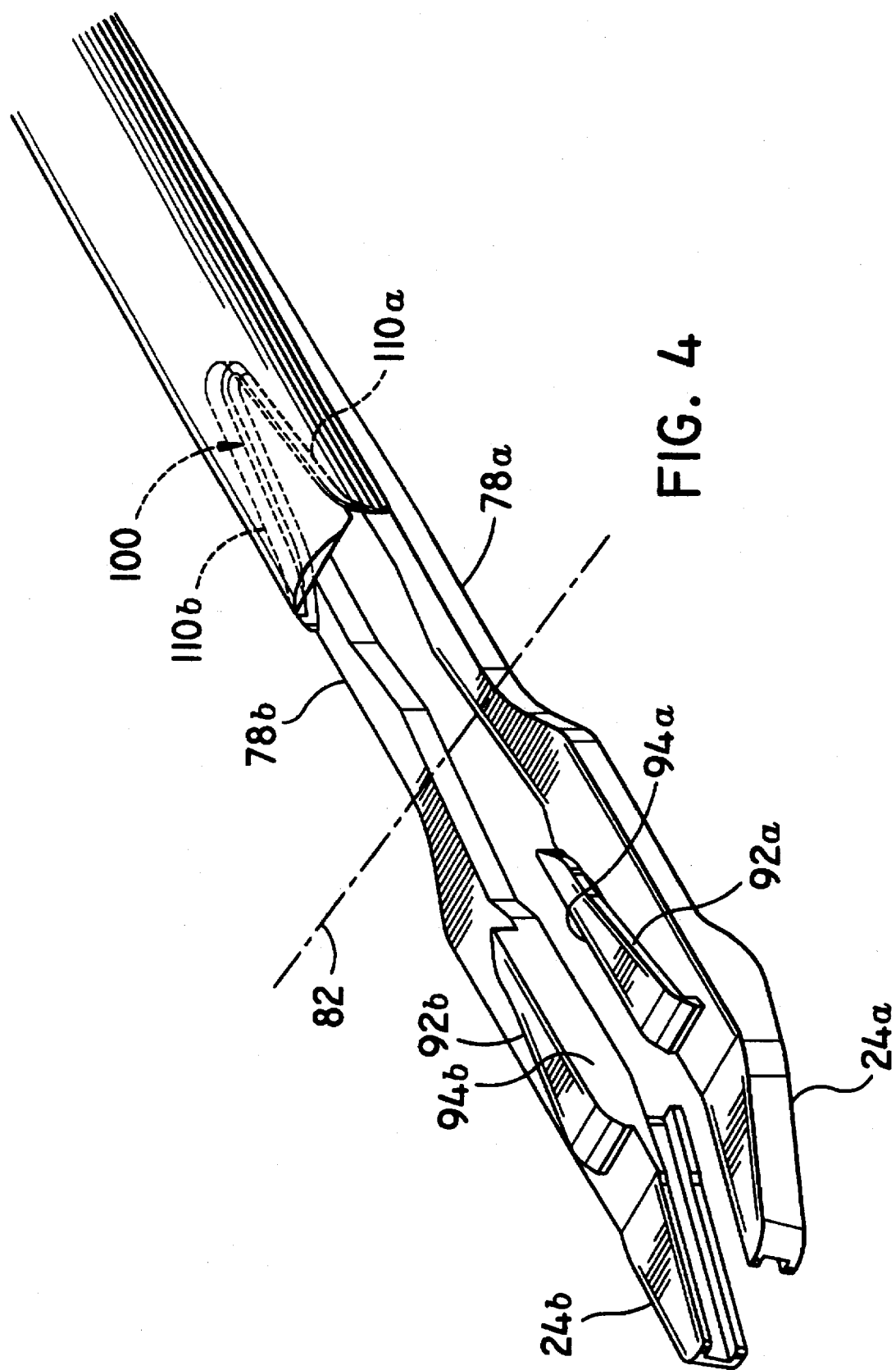
FIG. 4 is an enlarged perspective view from below of the subject clip applier, illustrating camming surfaces on jaw portions.

Turning now to FIG. 4, each of jaw portions 24a and 24b includes raised camming surfaces 92a and 92b formed on the bottom surface thereof. In order to provide increased closing force, camming surfaces are disposed at a distal portion of jaw portions 24a and 24b adjacent inner surfaces 94a and 94b of jaw portions 24a and 24b.

Thrust Bar Subassembly

Referring to FIG. 5, thrust bar 72 extends along a substantial length of body portion 20. Distal portion 96 of thrust bar 72 has a semicircular cross-section and includes dual camming structure for opening and closing jaw portions 24a and 24b. First, channel structure 98 is configured with a racetrack-shaped groove pattern to control and cam jaw portions 24a and 24b to a spaced-apart position and maintain the jaw portions in the spaced-apart position. Second, jaw closure structure 100 includes a bifurcated cam configuration to approximate jaw portions 24a and 24b about a surgical clip.

As illustrated in FIG. 5A, channel structure 98 includes raised center block 102, having distal nose portion 103. Distal zone or recess 104 is disposed distal to center block 102. A pair of longitudinally elongated parallel channels 106a and 106b extend along the sides of center block 102. Proximal zone or recess 108 is disposed proximal to center block 102. Position tabs 90a and 90b of jaw assembly 18 are configured to slide within channel structure 98.

Jaw closure structure 100 includes a bifurcated configuration having a pair of camming surfaces 110a and 110b in a tapering V-shaped configuration to cooperate with raised camming surfaces 92a and 92b on jaw assembly 18. In particular, distal movement of thrust bar 72 moves camming surfaces 110a and 110b into surrounding arrangement with respect to raised camming surfaces 92a and 92b, thereby moving jaw portions 24a and 24b into approximation.

A proximal portion of thrust bar 72 includes trip lever assembly 112. Trip lever assembly 112 includes trip lever 114 mounted on thrust bar 72 and disposed within longitudinally aligned recess 116. Trip lever 114 is rotatably retained therein by pivot pin 118 passing through transverse aperture 120. Distal tab 122 of trip lever 114 is normally biased upward by trip lever spring 124 disposed within cylindrical recess 126. It is contemplated that the trip lever and spring arrangement could be substituted with other equivalent structure including, e.g., a leaf spring or other resilient member.

A hemispherical portion 128 of thrust bar 72 having a flat upper surface is provided distal to the trip lever assembly 112. Both hemispherical portion 128 and trip lever assembly 112 are configured to engage with clip advancement subassembly 130 as will be described below.

Clip Advancement Subassembly

Turning now to FIG. 6, clip advancement subassembly 130 is depicted including upper housing 132, lower housing 134, and clip advancer or clip pusher 136. Upper housing 132 and lower housing 134, in combination, define a feed chute sized and configured to facilitate the stacking of surgical clips. With reference to FIG. 7, upper housing 132 has a substantially semicircular cross-section and includes groove 138 and recess 140. FIG. 8 illustrates lower housing 134 which includes base portion 142 and side walls 144a and 144b. An upstanding flange or clip stop 146 is provided at the distal portion of lower housing 134.

Referring now to FIG. 9, upper housing 132 is connected to lower housing 134 and together define a semicircular cross-section. Substantially rectangular feed chute 148 is defined by upper housing 132 and by side walls 144a and 144b and base portion 142 of lower housing 134. As shown in FIG. 6, feed chute 148 stores a stack 150 of U-shaped surgical clips 152 therein, including a distalmost surgical clip 152a. Surgical clip stack 150 is configured such that legs 154c of surgical clip 152c are substantially in contact with the crown portion 156b of the next distal surgical clip 152b. The stack 150 of surgical clips 152 is urged towards the distal portion of feed chute 148 by clip follower 158 which is biased distally by follower spring 160 positioned in recess 140 of upper housing 132. The proximal end of spring 160 is retained by retainer block 162 disposed adjacent flange 164 of lower housing 134. Clip stop 146 inhibits a distalmost surgical clip 152a from moving into the jaw assembly 18 by contacting the crown portion 156a of surgical clip 152a.

Clip pusher 136 slides along groove 138 formed on an upper surface of upper housing 132. During a portion of the closing stroke of movable handle 14, clip pusher 136 is distally advanced by thrust bar 72, as will be described below. Clip pusher 136 is biased proximally by return spring 166. A distal end of return spring 166 is retained by retainer block 162. With reference to FIG. 10, the proximal end of return spring 166 surrounds supporting pin 168 which is retained by flange 170 in clip pusher 136.

With reference to FIG. 11, the distal end portion of clip pusher 136 includes an angularly depending portion 172 including a bifurcated clip engaging portion 174 having a leading edge 176 and a sloping trailing edge 177.

Turning now to FIG. 12, the various components of clip advancement subassembly 130 are illustrated in combination. In particular, upper housing 132 and lower housing 134 are assembled. Clip pusher 136 is slidably mounted on upper housing 132 and biased proximally by return spring 166.

FIG. 12A illustrates in enlarged form the position of distalmost surgical clip 152a at the distal end of feed chute 148. Legs 154a of surgical clip 152a are stabilized by side walls 144a and 144b, and crown 156a is supported by clip stop 146. Angularly depending portion 172 of clip pusher 136 extends into feed chute 148. Leading edge 176 of clip engaging portion 174 is configured to contact crown 156a of surgical clip 152a to advance the clip beyond clip stop 146 as will be described below.

Figure 13:
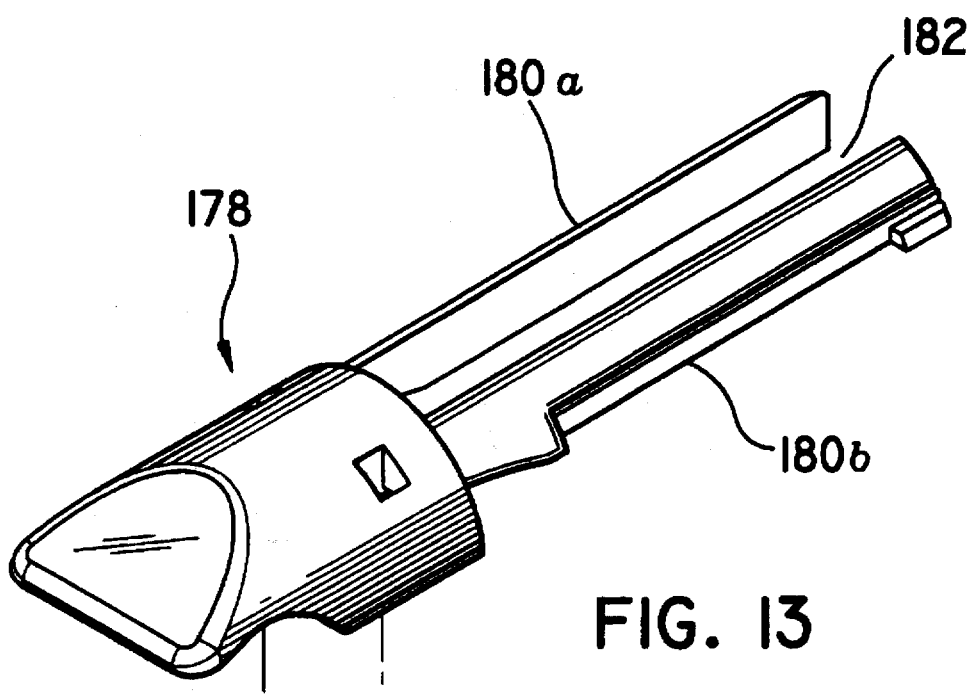
FIG. 13 is an enlarged perspective view with parts separated of a preferred nosepiece of the subject surgical clip applier.
Figure 14:
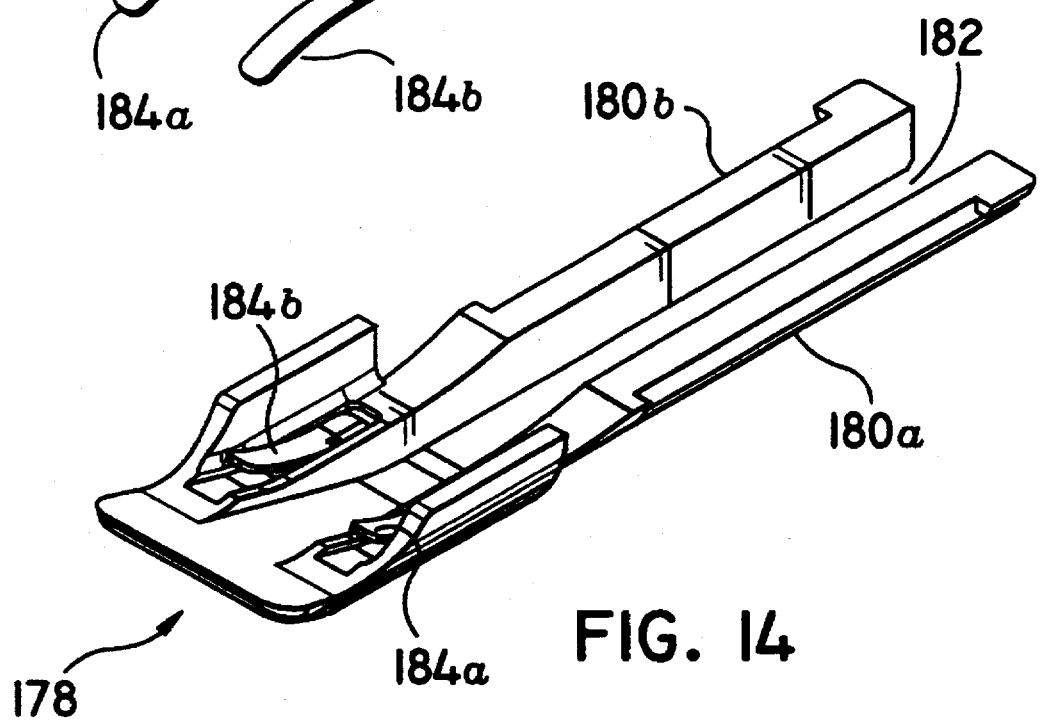
FIG. 14 is an enlarged perspective view from below of the nosepiece.

With reference to FIG. 13 in conjunction with FIG. 14, nosepiece 178 includes a pair of proximally extending members 180a and 180b defining a longitudinal slot 182 therebetween to direct angularly depending portion 216 of clip pusher 140. A pair of resilient tabs 184a and 184b are mounted on the bottom portion of nosepiece 178 to apply a downward force on jaw portions 24a and 24b to provide positive engagement of the jaw portions with camming structures 98 and 100 on thrust bar 72.

Method of Assembly

Having thus described the internal components and/or subassemblies of instrument 10, the method of assembly will now be described. With reference to FIG. 20, endo- scopic portion 20 is assembled from the previously described components.

Jaw assembly 18 is positioned adjacent distal portion 96 of thrust bar 72 such that position tabs 90a and 90b are disposed within channel structure 98.

Figure 15:
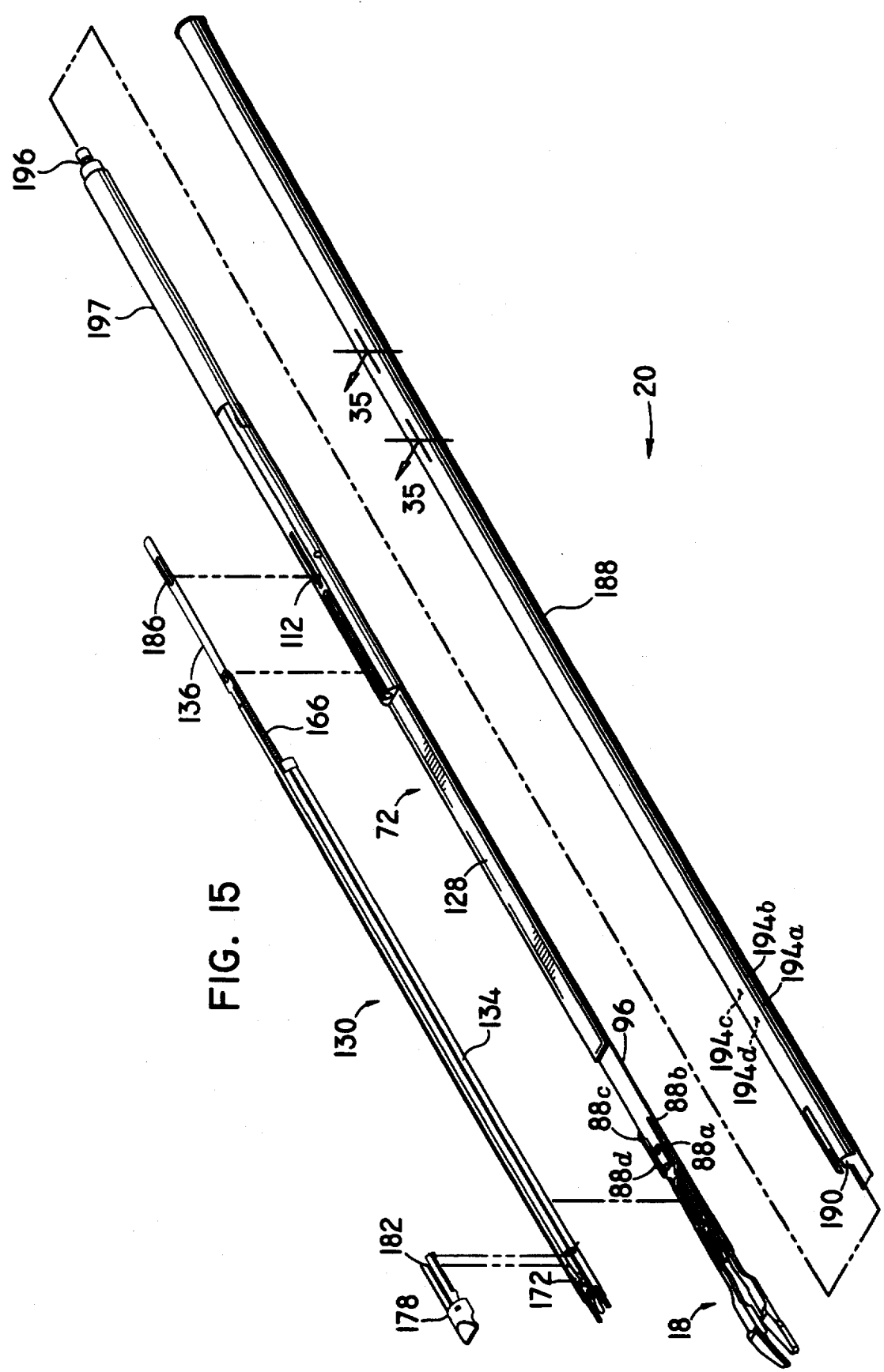
FIG. 15 is a perspective view of the subject surgical clip applier with subassemblies separated, illustrating the nosepiece, the clip advancement subassembly, the thrust bar, the jaw assembly, and the outer sleeve.
Figure 16:
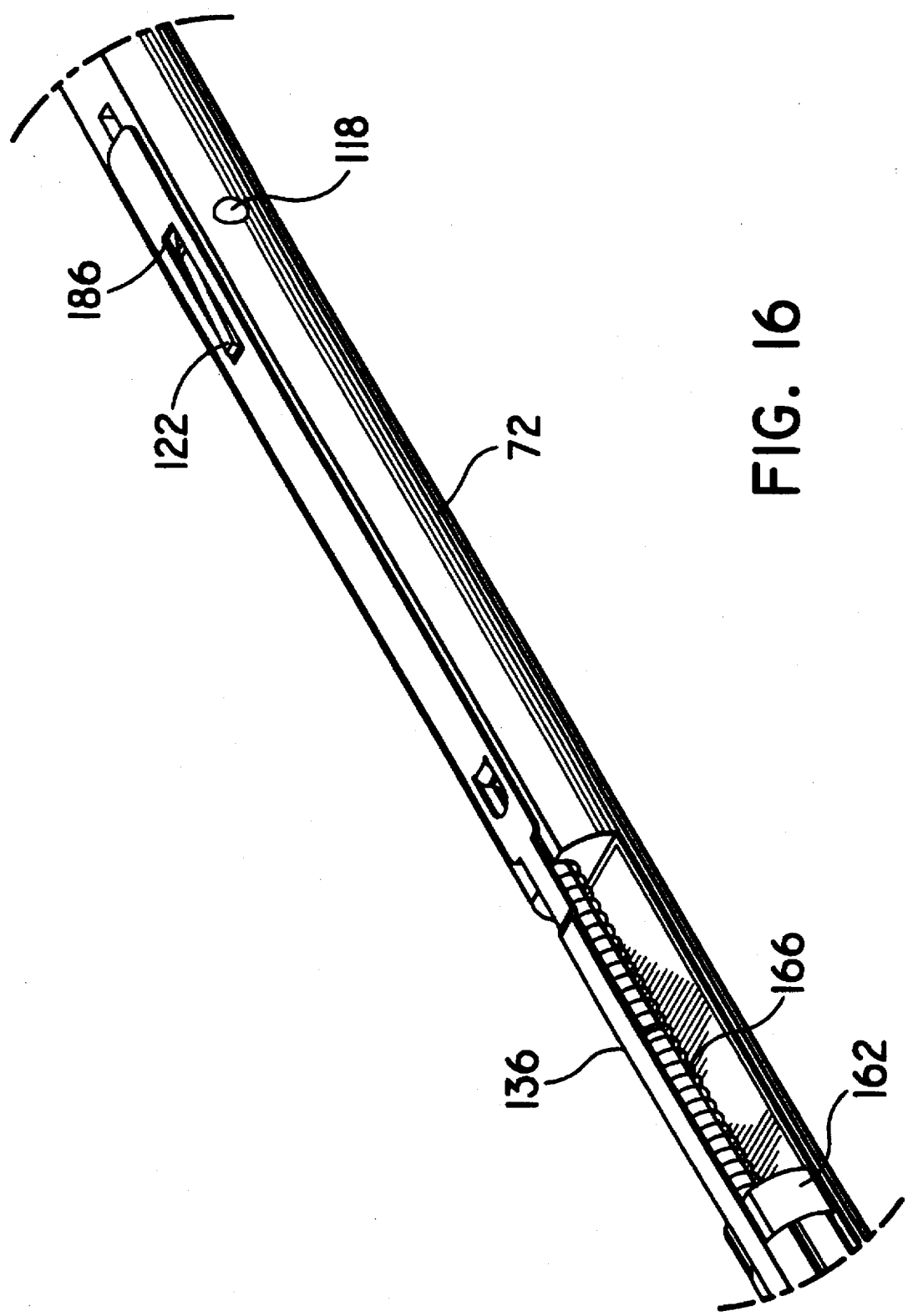
FIG. 16 is an enlarged perspective view of the endoscopic portion, illustrating an interlocking mechanism between the thrust bar and the clip pusher.

At the distal portion of clip advancement subassembly 130, nosepiece 178 is positioned adjacent lower housing 134 such that angularly depending portion 172 of clip pusher 136 is slidable within slot 182.

with reference to FIG. 15 in conjunction with FIG. 16, assembly of clip advancement subassembly 130 and thrust bar 72 will now be described. Base portion 142 of lower housing 134 is configured to rest partially on hemispherical portion 128 of thrust bar 72 and partially on jaw assembly 18. Longitudinal slot 186 at a proximal portion of clip pusher 136 is positioned in interlocking arrangement with trip lever assembly 112.

With continued reference to FIG. 15, a substantially cylindrical profile is defined by the combination of thrust bar 72, and clip advancement subassembly 130. Outer sleeve 188 is provided defining a cylindrical internal passage 190 therethrough having a circular cross-section. Internal passage 190 is sized to receive the assembled components described above, which are inserted into the distal end portion 192 of outer sleeve 188. Apertures 194a, 194b, 194c, and 194d at distal portion 192 of outer sleeve 188 are configured to receive tabs 88a, 88b, 88c, and 88d of jaw assembly 18 in snap-fitting arrangement.

Turning now to FIGS. 17 and 18, the assembly of endoscopic portion 20 and handle portion 12 will now be described. Bifurcated distal portion 68 of pusher plate 36 is connected to a proximal mounting portion 197 of thrust bar 72. In particular, annular notch 196, is configured to be received by prongs 70a and 70b for angular rotation of thrust bar 72 with respect to pusher plate 36. Rotation knob (not shown) is slidable over this junction to prevent separation of the thrust bar 72 from pusher plate 36.

Overall Operation of Instrument

Having thus described the internal components and assembly of instrument 10, the operation of the instrument will now be described. With reference to FIGS. 19 and 20, instrument 10 is initially disposed with movable handle 14 in the open or "at-rest" position. As illustrated in FIGS. 21–22, position tabs 90a and 90b of jaw assembly 18 are disposed in channel structure 98, and more particularly in distal zone 104. Position tabs 90a and 90b are freely movable within the distal zone 104 as indicated by arm "B". Consequently, jaw portions 24a and 24b are freely movable between the spaced and the approximated positions. To facilitate insertion of jaw assembly 18 and endoscopic body portion 20 into a small diameter cannula, e.g., a 5 mm diameter cannula, jaw portions 24a and 24b may be manually approximated such that the jaw assembly 18 does not extend beyond the diameter of the outer sleeve 188, e.g., by the surgeon's fingers or by contact with the inner geometry of the 5 mm cannula. Movable handle 14 is maintained in the "at-rest" position during insertion of body portion 20 and jaw assembly 18 through the cannula.

When the surgeon has placed the jaw assembly 18 adjacent the surgical site, a single closing stroke of movable handle 14 towards stationary handle 16 is sufficient to first deploy and/or ensure that the jaw portions 24a and 24b are in a spaced apart position adjacent or around the tissue or structure to be crimped, to sequentially advance a clip to the spaced-apart jaw portions, to reposition the clip-containing jaw portions, as desired, and to finally deform the clip on the desired structure. Closure from the "at-rest" position of movable handle 14 to a first intermediate position constitutes an initial throw thereof. Secondly, closure from the first intermediate position to a second intermediate position constitutes an intermediate throw. Finally, closure from the second intermediate position to the closed position constitutes a final throw.

During the initial throw of handle 14, the position of handle 14 is intermediate to that shown in FIG. 19 and FIG. 23. Thrust bar 72 moves distally, and position tabs 90a and 90b begin to contact distal nose portion 103 of center block 108. Consequently, position tabs 90a and 90b are sequentially conveyed into parallel channels 106a and 106b, respectively. Simultaneously, jaw portions are moved to the spaced apart position for reception of a surgical clip 152a.

Figure 25:
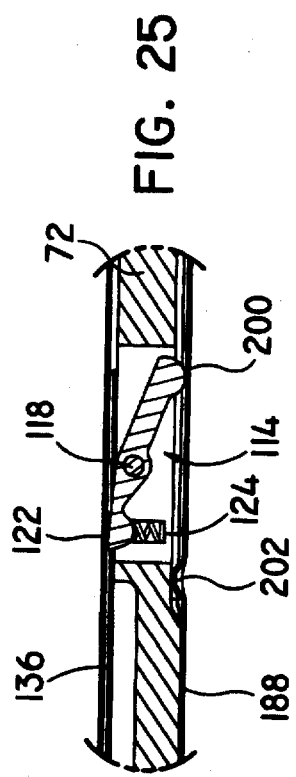
FIG. 25 is an enlarged cross-sectional view of the endoscopic portion, illustrating interlocking of a trip lever of the thrust bar with the clip pusher of the instrument in the progressive actuation position of FIG. 23.
Figure 26:
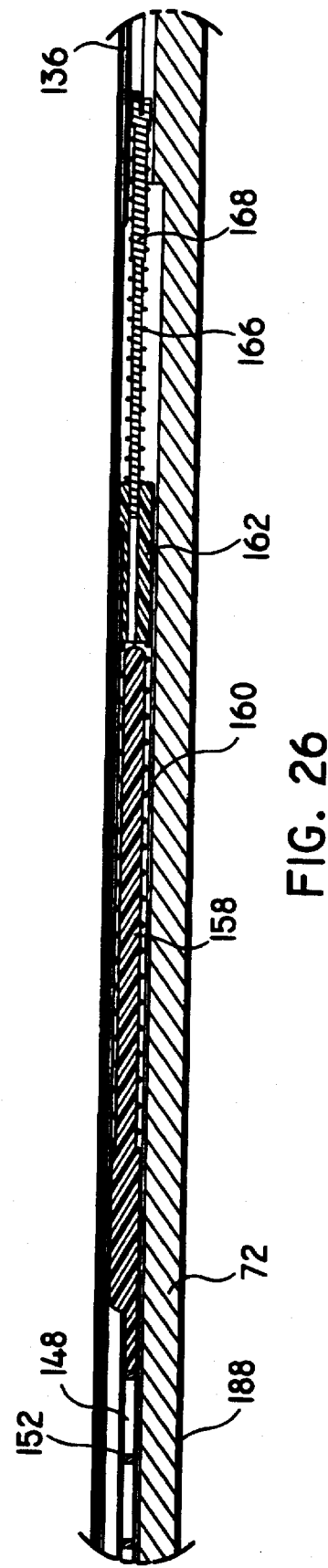
FIG. 26 is an enlarged cross-sectional view of the endoscopic portion, illustrating a feed chute, a clip follower, and a stack of surgical clips of the instrument in the progressive actuation position of FIG. 23.

The beginning of the intermediate throw is shown in FIGS. 23–30. As illustrated in FIG. 24, pawl 58 is in engagement with rack 54. With reference to FIG. 25, clip pusher 136 moves distally with thrust bar 72 due to locking engagement of distal tab 122 of trip lever 114 with slot 186 of clip pusher 136. FIG. 26 depicts clip follower 158 in biased relationship with the stack 150 of surgical clips 152.

In FIGS. 27–28, clip engaging portion 174 advances the crown 156a of the distalmost surgical clip 152a distally to overcome the restraining force of clip stop 146. Clip camming surface 198 contacts crown 156a and directs legs 154a of surgical clip 152a into channels 84a and 84b on the inner surfaces of jaw portions 24a and 24b.

FIGS. 29 and 30 show position tabs 90a and 90b ride in parallel channels 106a and 106b. Due to interposition of center block 102 between position tabs 90a and 90b, jaw portions 24a and 24b are maintained and controlled in the spaced apart position against opening or closure. In addition, the spacing of jaw portions 24a and 24b is selected such that a tight frictional grip is created between jaw portions 24a and 24b and surgical clip 152a to prevent surgical clip 152a from falling out of the jaw portions.

Figures 31, 32:
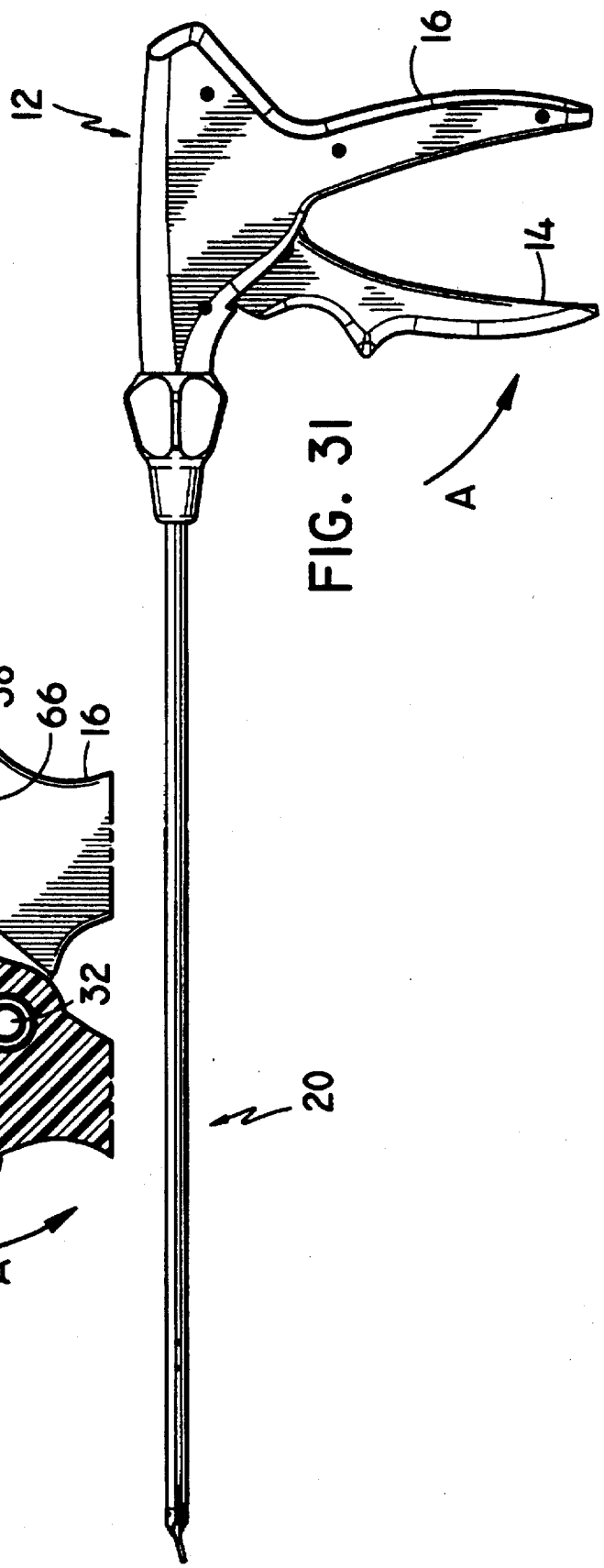
FIG. 31 is a side view of the subject surgical clip applier, illustrating the movable handle at the end of the intermediate throw of the closing stroke.
FIG. 32 is an enlarged cross-sectional view of the handle portion of the instrument in the actuation position of FIG. 31.
Figure 33:
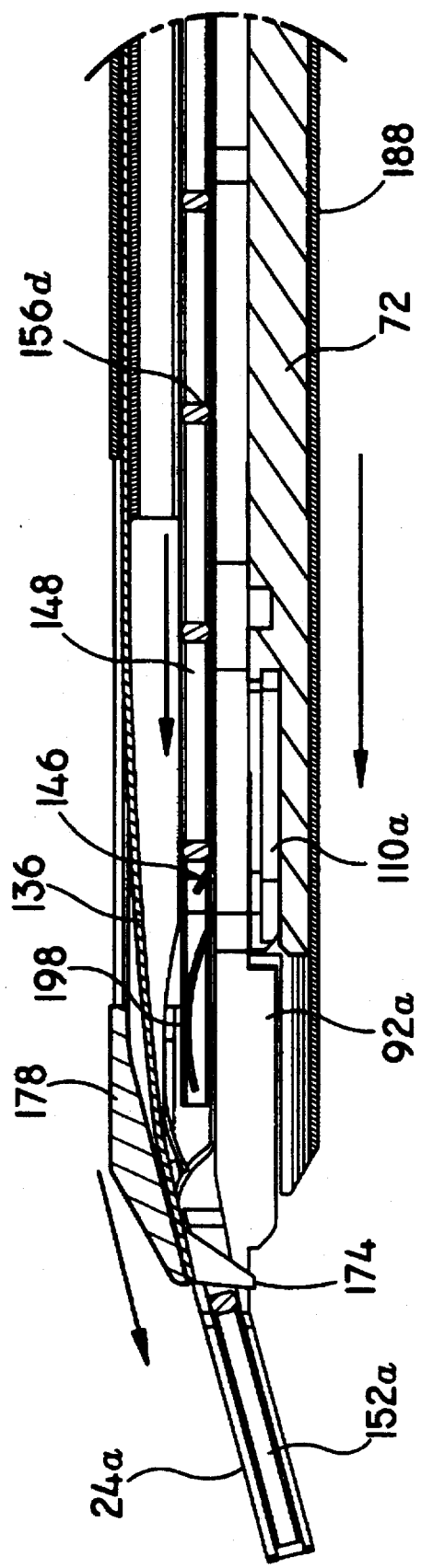
FIG. 33 is an enlarged cross-sectional view of the jaw assembly, illustrating the clip pusher advancing a surgical clip to the jaw portions of the instrument in the actuation position of FIG. 31.

Referring to FIGS. 31–37, the operation of the end portion of the intermediate stroke will now be described. As illustrated in FIG. 32, movable handle 14 continues to advance pusher plate 36 distally. Pawl 58 is engaged with the ratchet teeth 56 on rack 54 to index advancement of thrust bar 72 and to prevent distal movement thereof during clip advancement. As illustrated in FIG. 33, clip engaging portion 174 has advanced surgical clip 152a into channels 84a and 84b in the jaw portions.

Figure 34:
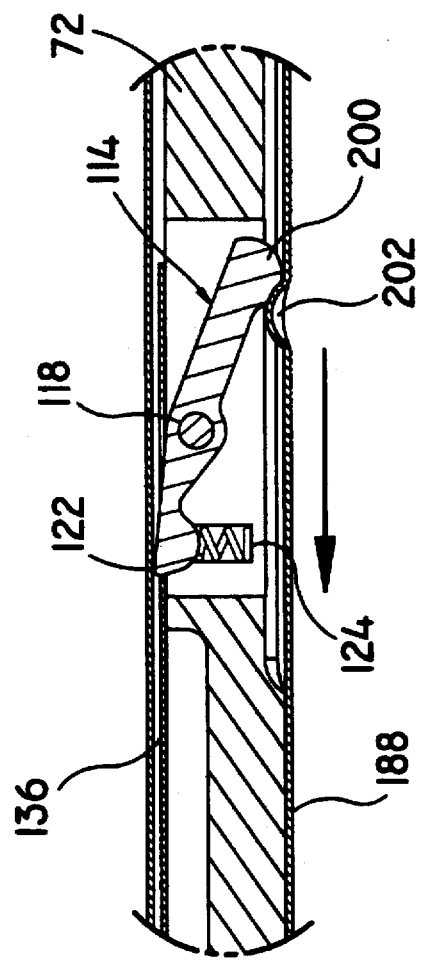
FIG. 34 is an enlarged cross-sectional view of the endoscopic portion, illustrating the trip lever of the thrust bar contacting a protrusion in the outer sleeve.
Figure 35:
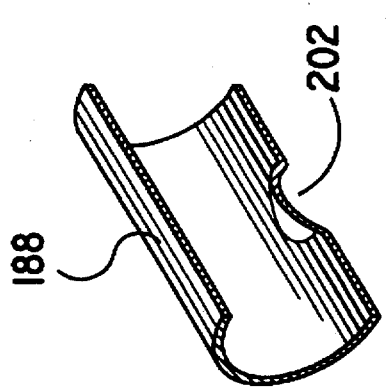
FIG. 35 is a perspective view of a hemispherical section of FIG. 15 taken along line 35—35 illustrating the protrusion formed in the outer sleeve portion.

Referring to FIG. 34, thrust bar 72 advances trip lever 114 such that proximal tab 200 contacts protrusion 202 on outer sleeve 188 (See, FIG. 35). As illustrated in FIG. 36, trip lever 114 pivots about pin 118 in the direction of arrow "C" against the bias of spring 124, and distal tab 122 moves downward and out of slot 186 in clip pusher 136. With reference to FIG. 37, clip pusher 136 returns proximally in the direction of arrow "P" due to the bias of return spring 166. The resilience of angled portion 172 and the shallow slope of trailing edge 177 enable clip engaging portion 174 to ride over crown 156b of the next surgical clip 152b.

Figure 38:
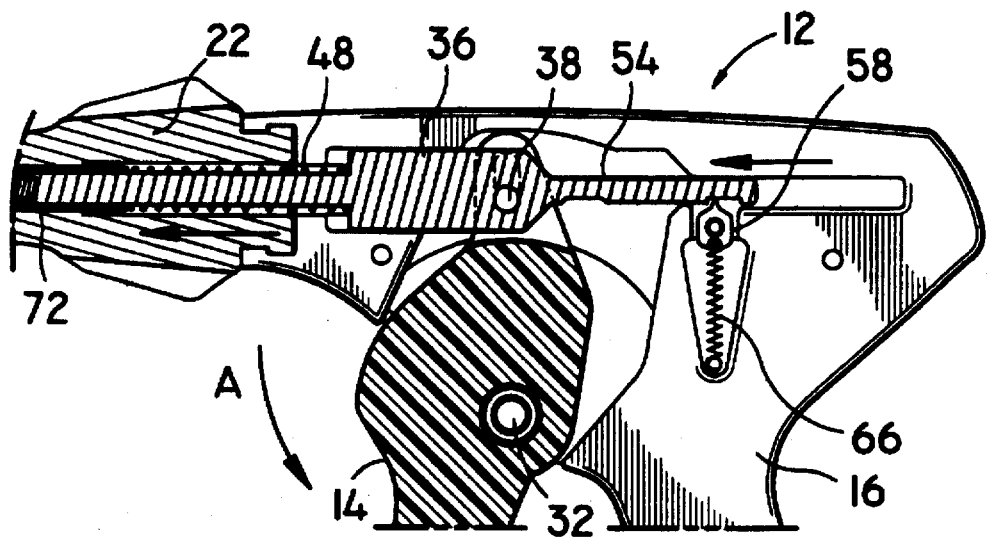
FIG. 38 is an enlarged cross-sectional view of the handle portion with the movable handle in the final throw of the closing stroke.
Figure 39:
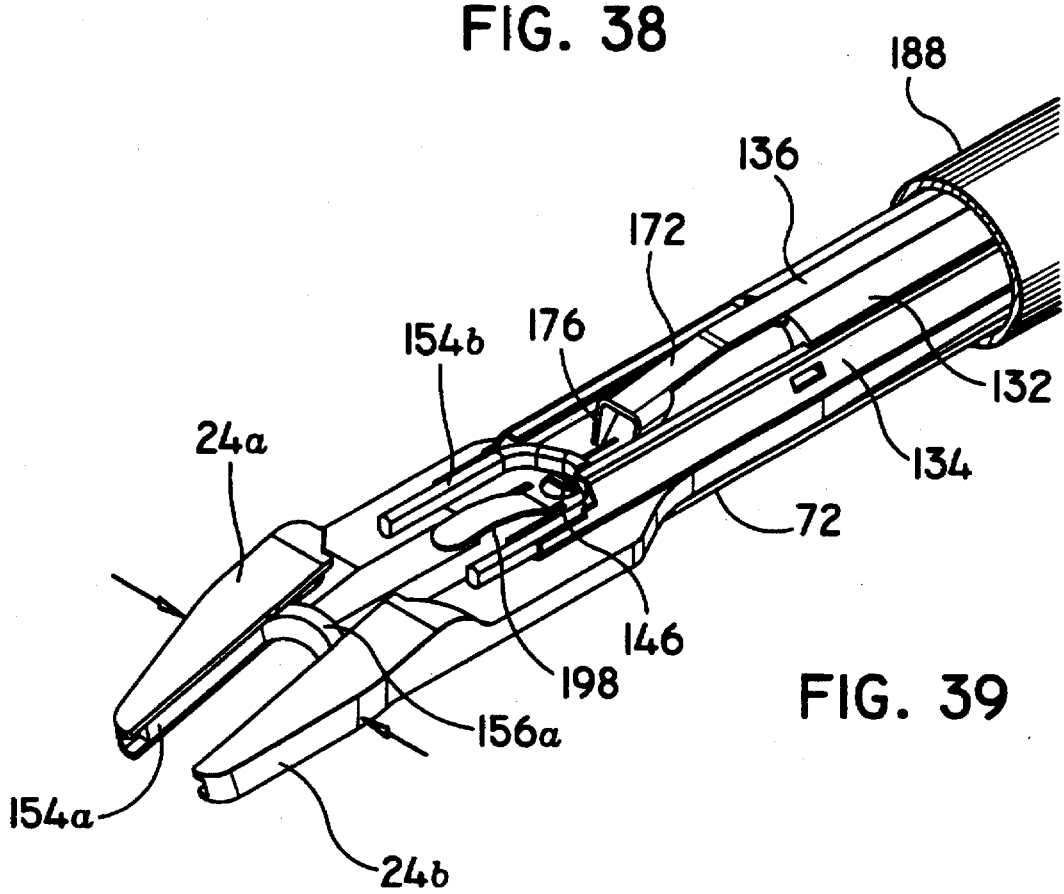
FIG. 39 is an enlarged perspective view of the jaw assembly, illustrating the closure of the jaw portions to deform the surgical clip disposed therebetween.

With reference to FIG. 38 in conjunction with FIG. 39, handle 14 is moved through the final throw towards the closed position. As illustrated in FIGS. 40–41, position tabs 90a and 90b pass from the parallel channels 106a and 106b to the proximal zone 108, in which jaw portions 24a and 24b are freely movable. Camming surfaces 110a and 110b on jaw closure structure 100 at the distal portion 96 of thrust bar 72 begin to engage raised camming surfaces 92a and 92b on jaw portions 24a and 24b. As illustrated in FIGS. 42–43, jaw portions 24a and 24b are gradually brought into approximation with distal movement of thrust bar 72. In particular, raised camming surfaces 92a and 92b are wider at the distal portion than at the proximal portion. Therefore, progressive movement of V-shaped jaw closure structure 100 cams jaw portions 24a and 24b closed. The proximity of jaw closure structure 100 and camming surfaces 92a and 92b to the distal portion of jaw portions 24a and 24b enables sufficient force to be exerted on jaw portions 24a and 24b to deform clip 152 and compress blood vessels or other body tissue surrounded thereby.

A Second Preferred Embodiment of the Subject Instrument

Turning now to FIGS. 44–49, another preferred embodiment of the clip applying instrument is disclosed at reference numeral 300. Instrument 300 operates substantially as described above with regard to instrument 10, with the differences described hereinbelow. In particular, FIG. 44 illustrates channel structure 302 disposed on thrust bar 304. Channel structure 302 includes raised center block 306 having a distal ridge portion 308 integral with thrust bar 304. In contrast to the channel structure 98 of instrument 10, the structure of distal ridge portion 308 is interposed in the space defined by distal zone 104 of instrument 10. A pair of channels 310a and 310b are defined surrounding center block 306 and proximal cavity or zone 312 is disposed proximal of center block 306. Channels 310a and 310b include distal angled channels 314a and 314b and longitudinally elongated parallel channels 316a and 316b.

Referring to FIG. 45, jaw assembly 318 includes elongated shank portions 320a and 320b having position tabs 322a and 322b. Position tabs 322a and 322b ride in channels 310a and 310b to control spacing of jaw portions 24a and 24b. When movable handle 14 is disposed in the "at-rest" position, position tabs 322a and 322b are positioned at the distal end of angled channels 314a and 314b. In this configuration, jaw portions 24a and 24b are restrained in an approximated position against opening for insertion through a cannula. In contrast with the channel structure 98 of instrument 10, the interposition of distal ridge structure 308 between position tabs 322a and 322b prevents movement of jaw portions 24a and 24b to the spaced apart position. Upon further closure of movable handle 14, thrust bar 304 is displaced distally and position tabs 322a and 322b traverse angled channels 314a and 314b. Jaw portions 24a and 24b are thereby cammed to the spaced apart configuration. Upon further closure of movable handle 14, position tabs 322a and 322b move within parallel channels 316a and 316b. The spacing of jaw portions 24a and 24b is therefore maintained against closure or opening.

Figure 46:
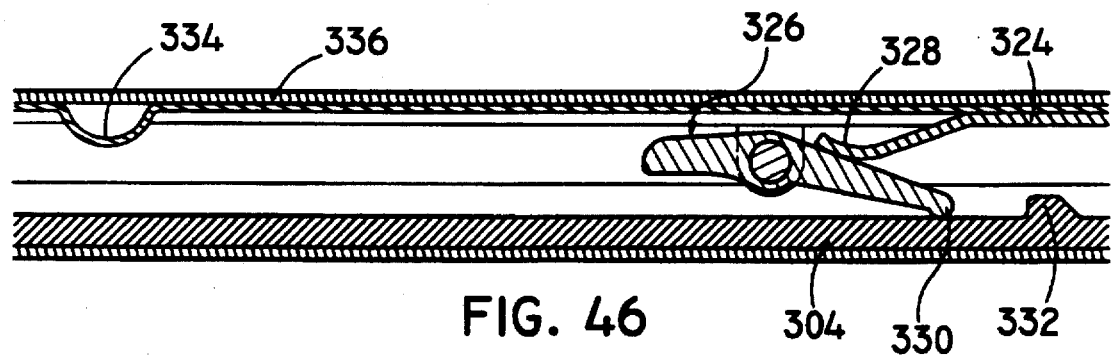
FIG. 46 is an enlarged cross-sectional view of the endoscopic portion of the embodiment of FIG. 44, illustrating initial spacing between a protrusion on the thrust bar and a trip lever on the clip pusher.
Figure 47:
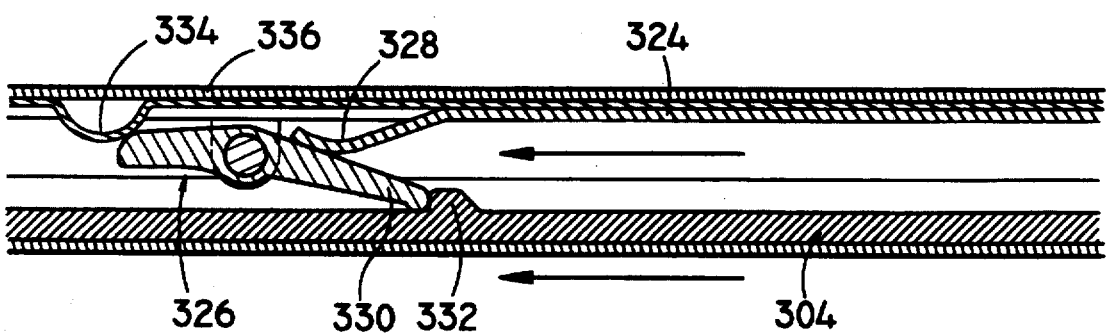
FIG. 47 is an enlarged cross-sectional view of the endoscopic portion, illustrating the thrust bar and clip pusher in engagement.

With reference to FIGS. 46–49, clip pusher 324 is biased proximally by return spring 186 as described above with respect to instrument 10. Clip pusher 324 includes a trip lever 326 disposed thereon for interlocking with thrust bar 304. This contrasts with instrument 10, wherein trip lever 114 is disposed on thrust bar 72. Trip lever 326 is normally biased by leaf spring 328 such that proximal tab 330 extends downward. A protrusion 332 is formed on thrust bar 304 to contact proximal tab 320. As illustrated in FIG. 46, protrusion 332 is spaced from trip lever 326 during the initial throw of movable handle 14. This configuration permits jaw portions 24a and 24b to be cammed open before a surgical clip is advanced into the jaw portions. Referring to FIG. 47, when jaw portions 24a and 24b are in the spaced-apart or open configuration, protrusion 332 on thrust bar 304 contacts downwardly extending trip lever 326 to advance clip pusher 324 with thrust bar 304.

Figure 48:
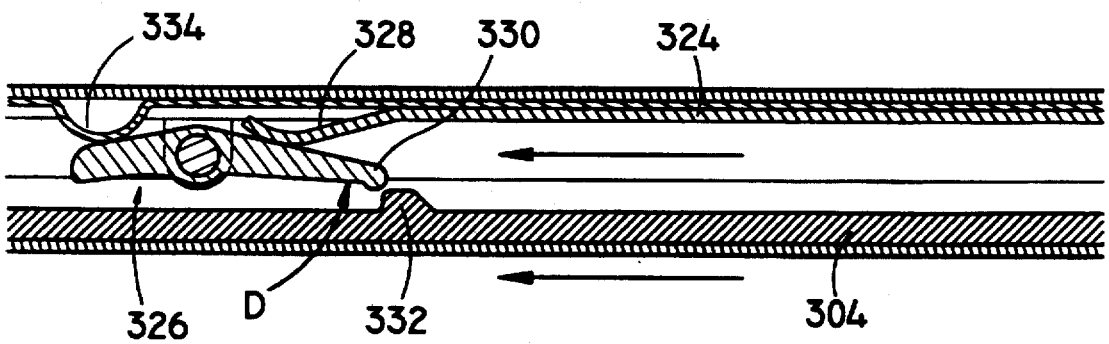
FIG. 48 is an enlarged cross-sectional view of the endoscopic portion, illustrating the trip lever pivoting against spring bias and out of engagement with the thrust bar.
Figure 49:
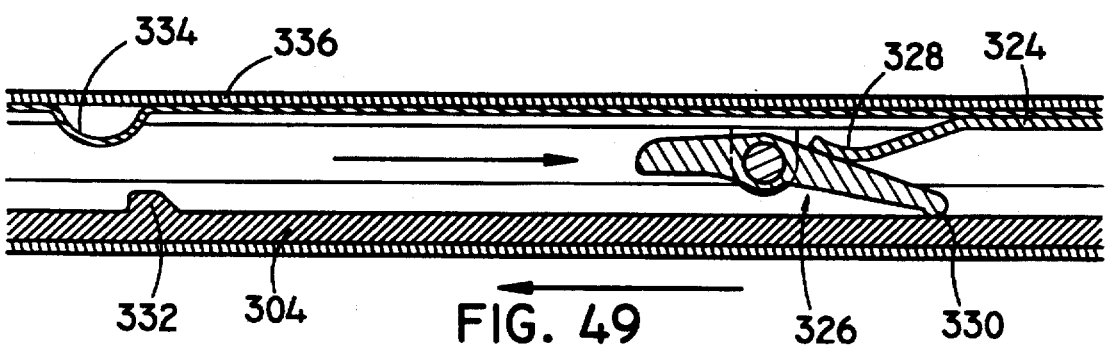
FIG. 49 is an enlarged cross-sectional view of the endoscopic portion, illustrating the clip pusher returning proximally.

As illustrated in FIG. 48, trip lever 326 contacts camming tab 334 disposed on outer tube 336 when clip pusher 324 has advanced the surgical clip into jaw portions 24a and 24b. Camming tab 334 pivots trip lever 326 against the bias of leaf spring 328 as shown by arrow "D". Proximal tab 320 moves upward and out of engagement with protrusion 332 on thrust bar 304. Consequently, FIG. 49 illustrates that return spring 166 moves clip pusher 324 proximally to permit closure of the jaw portions 24a and 24b to deform the clip.

It will be understood that various modifications may be made to the embodiments shown herein. For example, the jaw assembly and endoscopic portions may be sized to be accommodated in cannula assemblies of various sizes. Therefore, the above description should not be construed as limiting, but merely as exemplifications as preferred embodiments. Those skilled in the art will envision other modifications within the scope and spirit of the claims appended hereto.

What is claimed is:

1. An apparatus for endoscopic application of surgical clips to body tissue, which comprises:
    a) a handle portion including a first handle and a second handle mounted for relative movement and defining a single closing stroke between an open position and a closed position, the closing stroke including an initial throw, an intermediate throw, and a final throw;
    b) a body portion extending distally from the handle portion and defining a longitudinal axis;
    c) a plurality of surgical clips disposed within the body portion;
    d) a jaw assembly including first and second jaw portions mounted at the distal end portion of the body portion and movable between an approximated position and a spaced position;
    e) a jaw control mechanism operatively connected to the jaw assembly and configured to move the first and second jaw portions to the spaced position for reception of a distalmost clip in response to the initial throw of the handles, the jaw control mechanism configured to maintain the jaw portions in the spaced position during the intermediate throw of the handles, the jaw control mechanism configured to move the jaw assembly to the approximated position to deform the distalmost clip in response to the final throw of the handles; and
    f) a clip advancer mounted for operative association with the jaw control mechanism and configured to individually distally advance the distalmost clip to the jaw assembly during the intermediate throw of the handles.

2. An apparatus as recited in claim 1, further comprising a control assembly operatively connected to the jaw assembly and the handle portion for moving the first and second jaw portions between the spaced and the approximated positions when the pivoting handle is in the open position.

3. An apparatus as recited in claim 1, wherein the jaw assembly is restrained in the approximated position when the pivoting handle is in the open position.

4. An apparatus as recited in claim 1, wherein the jaw control mechanism is an actuator mounted for reciprocal longitudinal movement in response to movement of the pivoting handle.

5. An apparatus as recited in claim 4, wherein the actuator includes an angled camming structure for moving the jaw portions to the spaced position.

6. An apparatus as recited in claim 5, wherein the actuator includes a camming structure having parallel longitudinal slots defined thereon for maintaining the jaws in the spaced position.

7. An apparatus as recited in claim 1, wherein the jaw control mechanism includes a jaw closure assembly disposed adjacent a distal portion of the jaw assembly to cam the jaw portions to the approximated position.

8. An apparatus as recited in claim 7, wherein the jaw closure assembly includes a substantially bifurcated distal end portion.

9. An apparatus as recited in claim 8, wherein the jaw closure assembly further includes camming structure adjacent the bifurcated distal end portion.

10. An apparatus as recited in claim 9, wherein the jaw assembly further includes a camming surface disposed on a distal portion of each of the first and second jaw portions to cooperate with the jaw closure assembly.

11. An apparatus for endoscopic application of surgical clips to body tissue, which comprises:
 a) a handle portion including a stationary handle and a pivoting handle mounted for movement with respect to the stationary handle defining a closing stroke between an open position and a closed position;
 b) a body portion extending distally from the handle portion and defining a longitudinal axis;
 c) a plurality of surgical clips disposed within the body portion;
 d) a jaw assembly including first and second jaw portions and movable by the handle portion between a spaced configuration and an approximated configuration, said jaw assembly defining a proximal portion located proximal to a midline of the jaw assembly and a distal portion located distal to the midline of the jaw assembly;
 e) camming structure operatively connected to the handle for moving the jaw portions from an at least partially approximated configuration to the spaced configuration for reception of a distalmost clip in response to partial closure of the pivoting handle;
 f) jaw closure assembly disposed adjacent the distal portion of the jaw assembly to move the jaw portions to the approximated configuration to deform the distalmost clip in response to full closure of the pivoting handle; and
 g) a clip advancer connected to the jaw assembly for individually distally advancing the distalmost clip when the jaw portions are in the spaced configuration.

12. An apparatus as recited in claim 11, wherein the camming structure is configured to maintain the jaw portions in the spaced configuration during at least a portion of the closing stroke of the pivoting handle.

13. An apparatus as recited in claim 12, wherein the camming structure includes parallel longitudinal slots.

14. An apparatus as recited in claim 11, wherein the jaw closure assembly includes a bifurcated distal portion.

15. An apparatus as recited in claim 14, wherein the jaw closure assembly includes a camming surface adjacent the bifurcated distal end portion to move the jaw portions to the approximated configuration.

16. An apparatus as recited in claim 15, wherein the camming surface of the jaw closure assembly cooperates with camming surfaces on the first and second jaw portions.

17. An apparatus as recited in claim 11, further comprising camming structure engageable with the jaw assembly for moving the jaw portions between the spaced and the approximated configurations when the pivoting handle is in the open position.

18. An apparatus as recited in claim 11, further comprising camming structure engageable with the jaw assembly for restraining the jaw portions in the approximated position when the pivoting handle is in the open position.

19. An apparatus for endoscopic application of surgical clips to body tissue, which comprises:
 a) a handle portion including a pivoting handle movable with respect to a stationary handle and defining a closing stroke between an open position and a closed position;
 b) a body portion extending distally from he handle portion;
 c) a plurality of surgical clips disposed within the body portion;
 d) a jaw mechanism including first and second jaws and a control assembly connected to the pivoting handle for effecting free movement of the jaws between a first configuration wherein the first and second jaws are freely movable between an approximated position and a spaced apart position, a second configuration wherein the first and second jaws are restrained in a spaced apart position for the reception of a distalmost clip and a third configuration wherein the first and second jaws are moved towards the approximated position to deform the distalmost clip, the first and second jaws being sequentially moved from the first configuration to the second configuration to the third configuration in response to the closing stroke of the pivoting handle; and
 e) a clip advancer operatively associated with the jaw mechanism for individually distally advancing the distalmost clip from the body portion in response to movement of the pivoting handle.

20. An apparatus for endoscopic application of the surgical clips to body tissue, which comprises:
 a) a handle portion including a pivoting handle movable with respect to a stationary handle and defining a closing stroke between an open position and a closed position;
 b) a body portion extending distally from the handle portion;
 c) a plurality of surgical clips disposed within the body portion;
 d) a jaw mechanism including first and second jaws and a control assembly connected to the pivoting handle for allowing said jaws to be freely movable between a first configuration wherein the first and second jaws are restrained in an approximated position, a second configuration wherein the first and second jaws are restrained in a spaced apart position for the reception of a distalmost clip and a third configuration wherein the first and second jaws are moved towards the approximated position to deform the distalmost clip disposed therebetween, the first and second jaws being sequentially moved from the first configuration to the second configuration to the third configuration in response to the closing stroke of the pivoting handle; and
 e) a clip advancer operatively connected to the jaw mechanism for individually distally advancing the distalmost clip from the body portion in response to movement of the pivoting handle.

21. In an apparatus for endoscopic application of surgical clips to body tissue having a handle portion for the actuation of a jaw assembly including first and second jaw portions configured to receive and deform such clips therein, the improvement comprising:
 a jaw control mechanism having a control assembly connected to the handle portion and configured to move the first and second jaw portions sequentially to a first configuration wherein the jaw assembly is freely movable, a second configuration wherein the jaw assembly is configured to maintain the jaw portions in a spaced apart position and a third configuration wherein the jaw assembly is moved to an approximated position in response to a single actuation of the handle portion.

22. A method for assembly of a surgical instrument, which comprises:

a) providing a handle assembly having a driver member mounted for longitudinal movement in response to actuation of the handle subassembly;

b) providing a control subassembly responsive to actuation of the handle assembly to define an initial throw, an intermediate throw, and a final throw of the handle assembly:

c) providing an actuator subassembly including a proximal mounting portion for engagement with said driver member and a distal mounting portion;

d) providing a tool subassembly having a proximal mounting portion configured to engage the distal mounting portion of said actuator subassembly; and e) sequentially assembling the control subassembly in operative engagement with the handle subassembly, assembling the actuator subassembly with the handle subassembly such that the proximal mounting portion of the actuator subassembly is in engagement with the driver member and assembling the actuator subassembly with the tool subassembly such that the proximal mounting portion of the tool assembly is in engagement with distal mounting portion of the actuator subassembly.

23. A method for assembly as recited in claim 22, wherein the surgical instrument is a clip applier and the tool subassembly is a pair of jaws, the method further comprising:

providing a clip advancement subassembly for advancing a clip and engagement structure for operatively engaging the driver member; and assembling the clip advancement subassembly to the handle subassembly such that the engagement structure of the clip advancement subassembly is operatively engaged with the driver member.

24. A method for assembly as recited in claim 23, wherein the method further comprises:

providing an elongated sleeve defining a longitudinal axis and an internal passage therethrough; and inserting the actuator subassembly and the clip advancement subassembly into the internal passage of the elongated sleeve.

25. A method for assembly as recited in claim 23, wherein at least a portion of the actuator subassembly has a semi-circular cross-section and the clip advancement subassembly has a semicircular cross-section, and the method further comprises:

providing an elongated sleeve defining a longitudinal axis and an internal passage therethrough, the elongated sleeve having a circular cross-section; and inserting the actuator subassembly and the clip advancement subassembly into the elongated sleeve to be slidably received within the circular cross-section thereof.

* * * * *